United States Patent
Schneck et al.

(10) Patent No.: US 6,734,013 B2
(45) Date of Patent: May 11, 2004

(54) USE OF MULTIVALENT CHIMERIC PEPTIDE-LOADED, MHC/IG MOLECULES TO DETECT, ACTIVATE OR SUPPRESS ANTIGEN-SPECIFIC T CELL-DEPENDENT IMMUNE RESPONSES

(75) Inventors: Jonathan Schneck, Silver Spring, MD (US); Drew Pardoll, Brookeville, MD (US); Sean O'Herrin, Baltimore, MD (US); Jill Slansky, Baltimore, MD (US); Tim Greten, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/789,720

(22) Filed: Feb. 22, 2001

(65) Prior Publication Data

US 2002/0006903 A1 Jan. 17, 2002

Related U.S. Application Data

(62) Division of application No. 09/150,622, filed on Sep. 10, 1998, now Pat. No. 6,268,411.
(60) Provisional application No. 60/082,538, filed on Apr. 21, 1998, and provisional application No. 60/058,573, filed on Sep. 11, 1997.

(51) Int. Cl.[7] .................. C12N 15/63; C07K 16/00; C12P 21/08
(52) U.S. Cl. ................. 435/320.1; 530/387.1; 530/388.1
(58) Field of Search ............... 435/320.1; 530/387.3, 530/388.1

(56) References Cited

U.S. PATENT DOCUMENTS

| | | | |
|---|---|---|---|
| 5,116,964 A | 5/1992 | Capon et al. | |
| 5,284,935 A | 2/1994 | Clark et al. | |
| 5,420,244 A | 5/1995 | Rudolph et al. | |
| 5,574,205 A | 11/1996 | Kucherlapati et al. | |
| 5,635,363 A | 6/1997 | Altman et al. | |
| 5,652,342 A | 7/1997 | Zimmerman et al. | |
| 5,679,641 A | 10/1997 | Melief et al. | |
| 5,820,866 A | 10/1998 | Kappler et al. | |
| 5,869,270 A | 2/1999 | Rhode et al. | |
| 6,011,146 A | 1/2000 | Mottez et al. | |
| 6,015,884 A | 1/2000 | Schneck et al. | |
| 6,268,411 B1 * | 7/2001 | Schneck et al. | |

FOREIGN PATENT DOCUMENTS

| | | | |
|---|---|---|---|
| EP | 0 352 761 | | 7/1989 |
| WO | WO 93/10220 | * | 5/1993 |
| WO | 93/10220 | | 5/1993 |
| WO | WO 93/17095 | | 9/1993 |

(List continued on next page.)

OTHER PUBLICATIONS

Casares et al. "Engineering and Characterization of a Murine MHC Class II–Immunoglobulin Chimera Expressing an Immunodominant CD4 T Viral Epitope" Protein Engineering, vol. 10, No. 11, Nov. 1997, pp. 1295–1301.

(List continued on next page.)

Primary Examiner—Anthony C. Caputa
Assistant Examiner—C. Yaen
(74) Attorney, Agent, or Firm—Banner & Witcoff, Ltd.

(57) ABSTRACT

To increase the effective affinity of soluble analogs of peptide/MHC molecules for their cognate ligands, divalent peptide/MHC complexes were constructed. Using a recombinant DNA strategy, DNA encoding the MHC class I was ligated to DNA coding for murine Ig heavy chain. MHC/Ig complexes were exploited to homogeneously load with peptides of interest. The results of flow cytometry demonstrated that the $^{pep}$MHC/Ig complexes bound specifically with high affinity to cells bearing their cognate receptors. $^{pep}$MHC/Ig complexes are also useful in modulating effector functions of antigen-specific T cells. These $^{pep}$MHC/Ig complexes are useful for studying TCR/MHC interactions and lymphocyte tracking and have uses as specific regulators of immune responses.

4 Claims, 24 Drawing Sheets

(1 of 24 Drawing Sheet(s) Filed in Color)

FOREIGN PATENT DOCUMENTS

| | | |
|---|---|---|
| WO | WO 93/24525 | 12/1993 |
| WO | 94/19473 A | 9/1994 |
| WO | WO 94/24290 | 10/1994 |
| WO | 94/26903 | 11/1994 |
| WO | 94/28871 | 12/1994 |
| WO | 96/04314 | 2/1996 |
| WO | 96/20215 | 7/1996 |
| WO | 97/35991 | 10/1997 |
| WO | WO 97/44667 | 11/1997 |
| WO | WO 98/03552 | 1/1998 |
| WO | WO 98/06749 | 2/1998 |
| WO | WO 98/10284 | 3/1998 |
| WO | WO 99/09064 | 2/1999 |
| WO | WO 99/42597 | 8/1999 |
| WO | WO 99/50637 | 10/1999 |
| WO | WO 99/64597 | 12/1999 |

OTHER PUBLICATIONS

Kalandadze et al. "Expression of Recombinant HLA–DR2 Molecules" The Journal of Biological Chemistry, Vol. 271, No. 33, Aug. 16, 1996, pp. 20156–20162.

Scott et al. "Role of Chain Pairing for the Production of Fucntional Soluble IA Major Histocompatibility complex Class II Molecules" J. Exp. Med. vol. 183, May 1996, pp. 2087–2095.

Gnjatic et al. "Mapping and ranking of potential cytotoxic T epitopes in the p53 protein: effect of mutations and polymorphism on peptide binding to purified and refolded HLA molecules" Eur. J. Immunol. 25(6):1638–42 (Jun. 1995) (Abstract).

Kozono et al., "Production of soluble MHC class II proteins with covalently bound single peptides" Nature 369(6476):151–54(May 1994).

Lee et al., "Functional cell surface expression by a recombinant single-chain class I major histocompatibility complex molecule with a cis–active beta 2–microglobulin domain" Eur. J. Immunol. 24(11):2633–39 (Nov. 1994) (Abstract).

Lepley et al., "Biochemical and Functional Characterization of Soluble Multivalent MHC $L^d$/Fcγ1 and $L^d$/Fcμ Chimeric Proteins Loaded with Specific Peptides" Transplantation, 63:765–774 (Mar. 15, 1997).

Lone et al. "In Vitro Induction of Specific Cytotoxic T Lymphocytes Using Recombinant Single–Chain MHC Class I/Peptide Complexes" J. Immunother. 21(4):283–294 (1998).

Mage et al. "A recombinant, soluble, single-chain class I major histocompatibility complex molecule with biological activity" PNAS 89(22):10658–62 (Nov. 1992).

McCarty et al. "Targeting p53 for adoptive T–cell immunotherapy" Cancers Res. 58, 2601–05 (Jun. 15, 1998) (Abstract).

McCarty et al. "An HLA–resistricted, p53 specific immune response from HLA transgenic p53 knockout mice" Ann Surg Oncol 1998 Jan.–Feb.;5(1):93–9.

Mottez et al. "Cells Expressing a Major Histocompatibility Complex Class I Molecule with a Single Covalently Bound Peptide are Highly Immunogenic" J. Exp. Med., 181:493–502 (Feb. 1995).

White et al. "Soluble Class I MHC with β–2Microglobulin Covalently Linked Peptides: Specific binding to a T Cell Hybridoma" J. Immunol. 162(5):2671–2676 (Mar. 1999).

Zwirner et al. "Expression of a Functional Chimeric Ig–MHC Class II Protein" J. Immunol. 148(1):272–6 (Jan. 1992).

Nijman et al. "Characterization of cytotoxic T lymphocyte epitopes of a self–protein, p53, and a non–self–protein, influenza matrix: relationship between major histocompatibility complex peptide binding affinity and immune responsiveness to peptides" J. Immunother 1993 Aug;14(2):121–6 (Abstract).

Vierboom et al. "Tumor eradiction by wild–type p53–specific cytotoxic T lymphocytes" J. Exp Med 1997 Aug 29;186(5):695–704 (Abstract).

Melief and Kast "T–cell immunotherapy of cancer" Res Immunol 1991 Jun.–Aug.; 142(5–6):425–9 (Abstract).

DeLeo "p53–based immunotherapy of cancer" Crit Rev Immunol 1998;18(1–2):29–35 (Abstract).

Bertholet et al. "Cytotoxic T lymphocyte repsonses to wild–type and mutant mouse p53 peptides" Eur J Immunol 1997 Mar.; 27(3):798–801 (Abstract).

Biggs et al. "Targeting p53 as a general tumor antigen" Proc Natl Acad Sci USA 1995 Dec 19, 1995;92(26):11993–7 (Abstract).

Mottez et al. "A single–chain murine class I major transplantation antigen" Eur J Immunol 1991 Feb;21(2):467–71.

J. Dal Porto et al. "A soluble divalent class I major histocompatibility complex molecule inhibits alloreactive T cells at nanomolar concentrations" Proceedings of the National Academy of Sciences vol. 90, 7/93 pp. 6671–6675.

T. Johansen et al. "Potent inhibition of alloreactive T cells by nanomolar concentrations of a divalent soluble class I MHC molecule" The Journal of Immunology, vol. 150, No. 8, part 2, Apr. 15, 1993, p. 83A.

C. Gregoire et al. "Engineered secreted T–cell receptor alpha–beta heterodimers" Proceedings of the National Academy of Sciences, vol. 88, Sep. 1991, pp. 8077–8081.

S. Weber et al. "Specific low–affinity recognition of major histocompatibility complex plus peptide by soluble T–cell receptor" Nature, vol. 356, Apr. 30, 1992, pp. 792–976.

H–C Chang et al. "A general method for facilitating heterodimeric pairing between two proteins: Application to expression of alpha and beta T–cell receptor extracellular segments" Proceedings of the National Academy of Sciences vol. 91, Nov. 1994, pp. 11408–11412.

S. O'Herrin and J.P. Schneck "Expression and analysis of soluble MHC– and TCR–immunoglobulin super dimers" The FASEB Journal, vol. 10, No. 6, Apr. 30, 1996 p. A1473.

J. Schneck et al. "Specific inhibition of graft rejection by soluble MHC superdimers" The FASEB Journal, vol. 10, No. 6, Apr. 30, 1996 p. A1473.

M. Lebowitz et al. "Specificity of soluble 2C TcR/Ig superdimers for peptide/MHC complexes" The FASEB Journal, Vol 10, No. 6, Apr. 30, 1996, p. A1178.

J. D. Altman et al. "Phenotypic Analysis of Antigen–Specific T Lymphocytes" Science, vol. 274, Oct. 4, 1996, pp. 94–96.

* cited by examiner

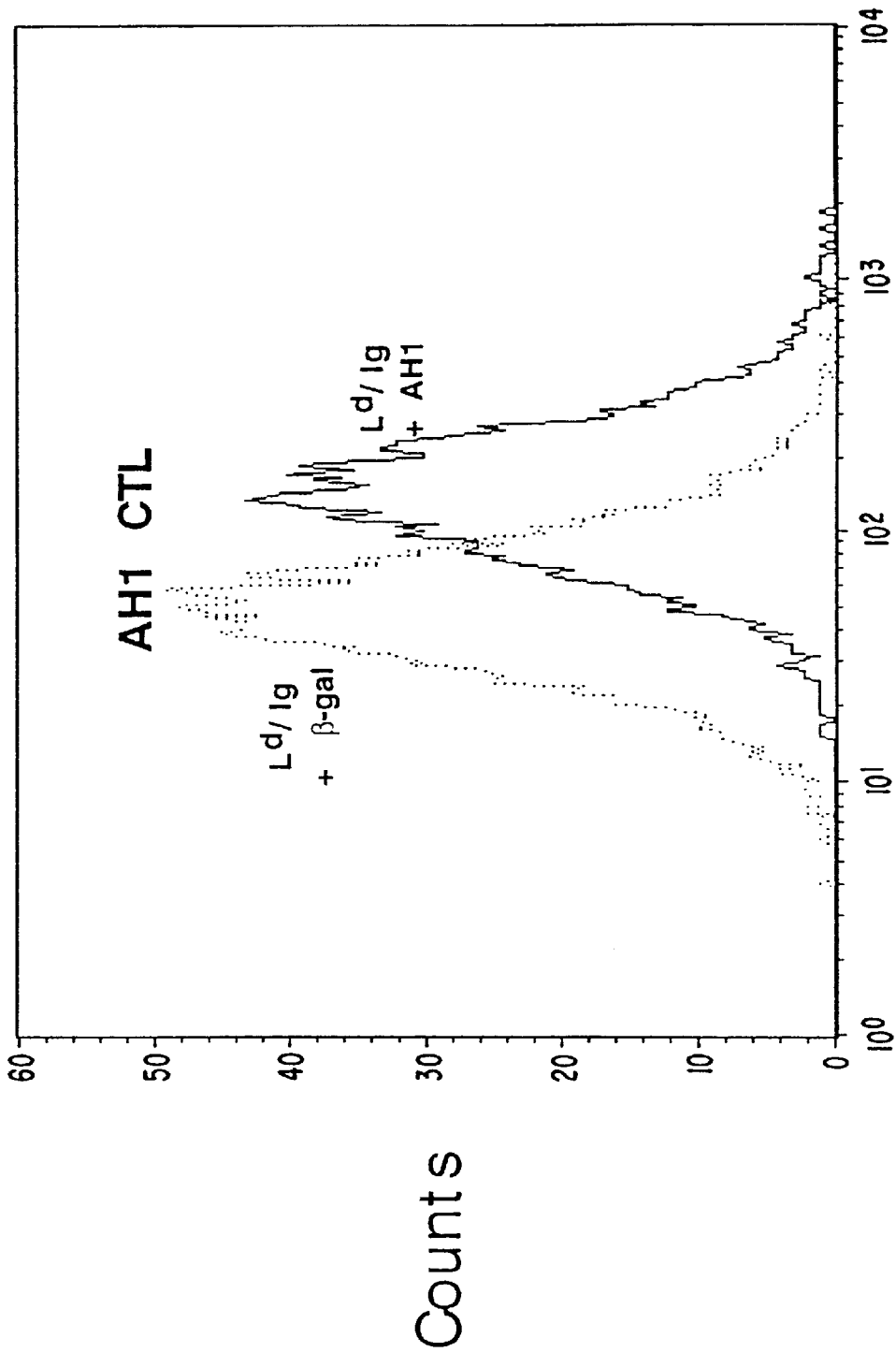

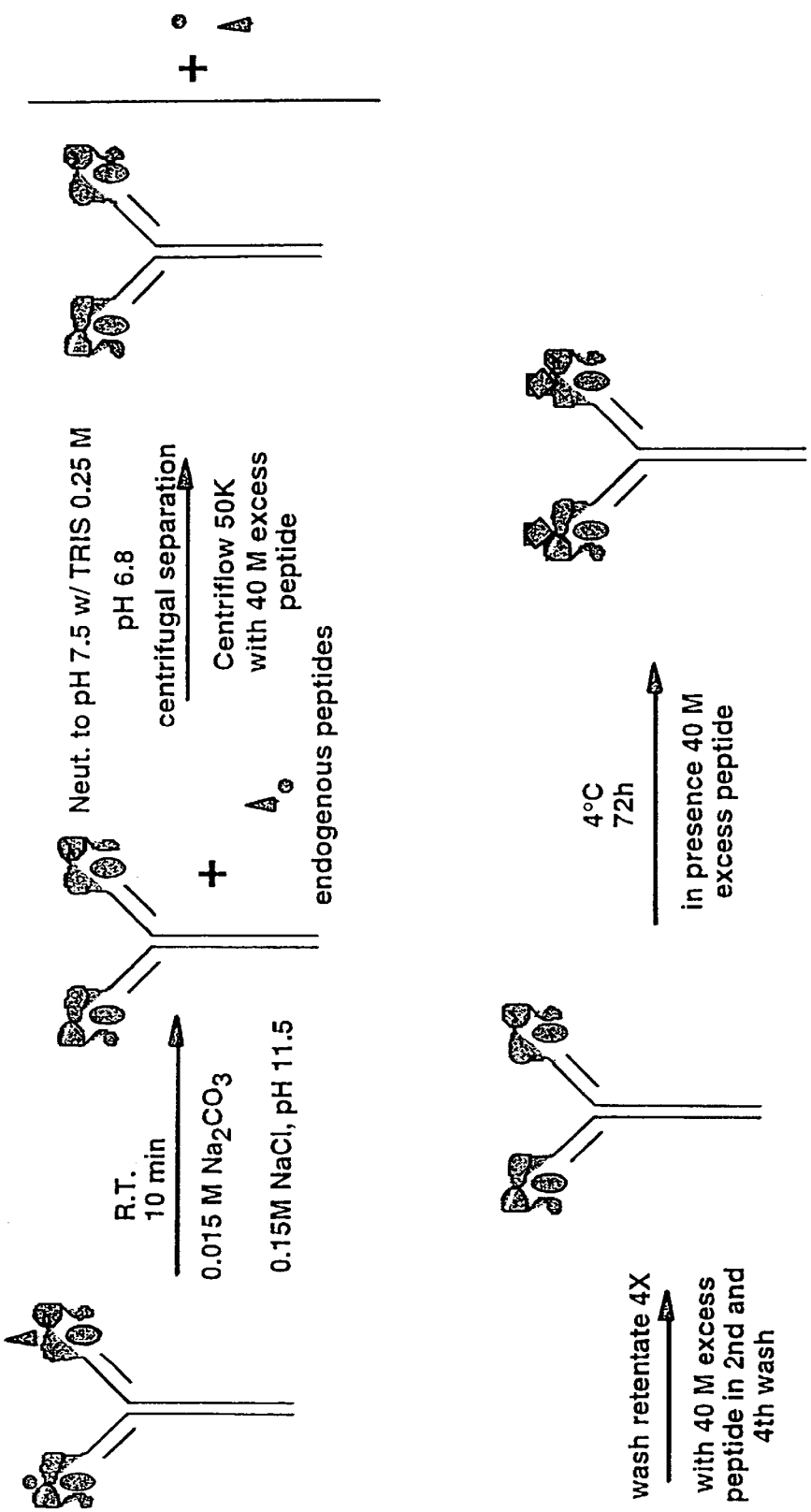

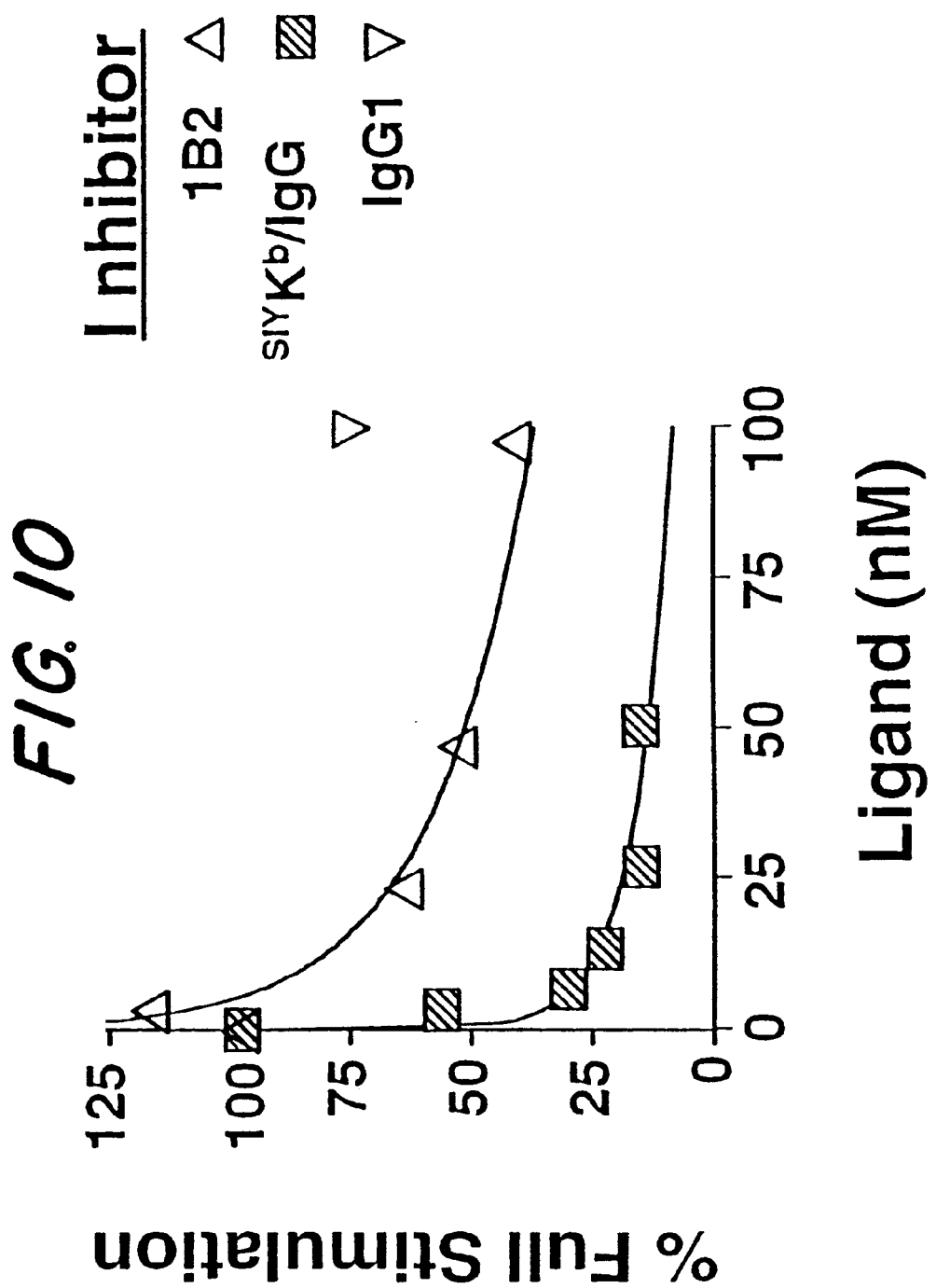

FIG. 14B
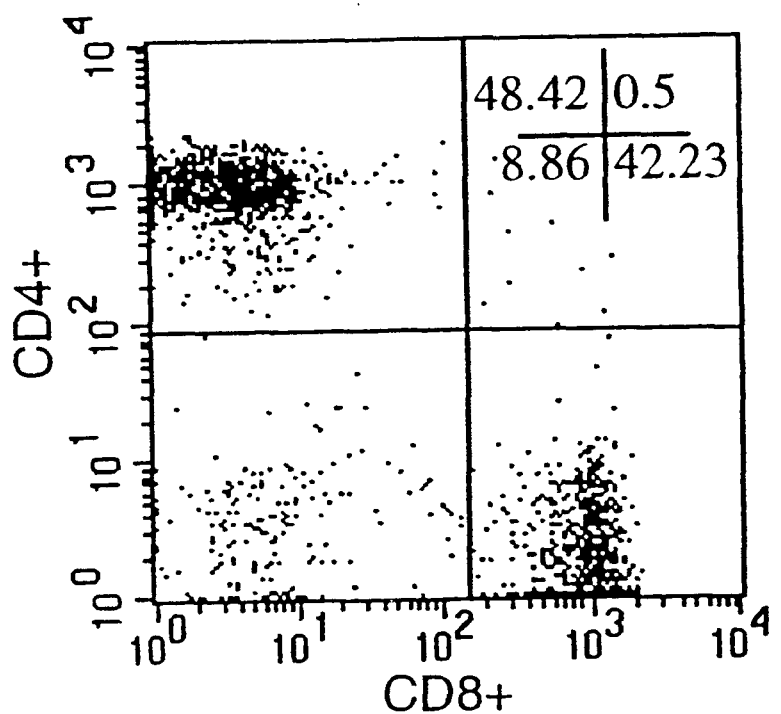
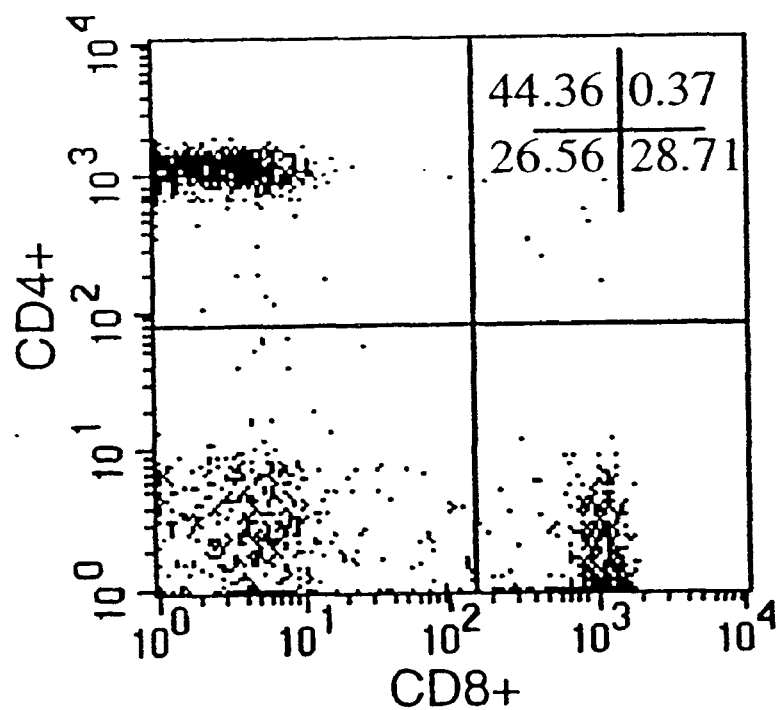

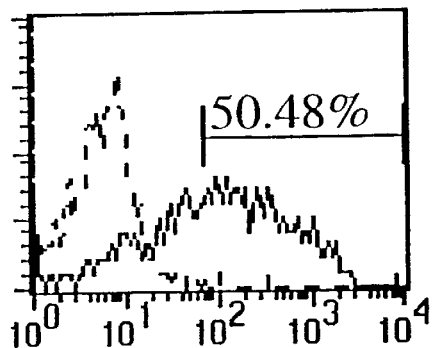
FIG. 15A
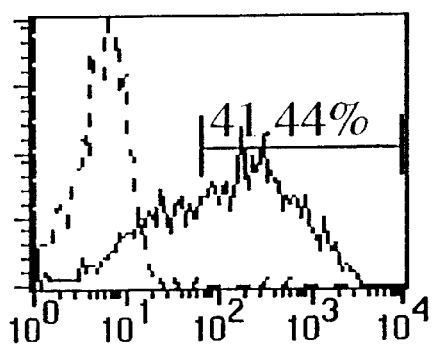
FIG. 15B
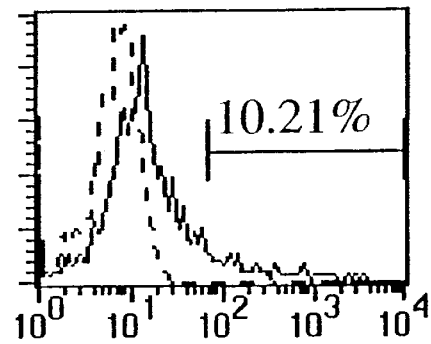
FIG. 15D
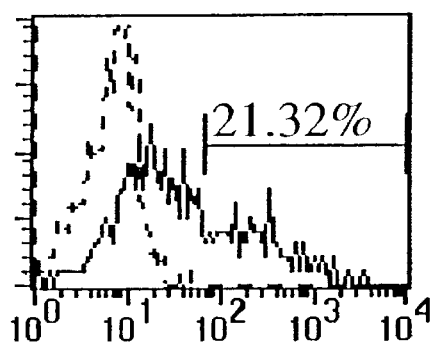
FIG. 15C
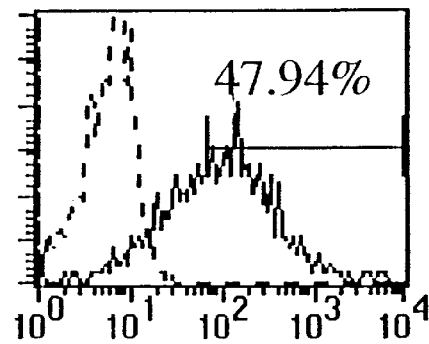
FIG. 15E
HLA-DR 

FIG. 16A
pt. H1
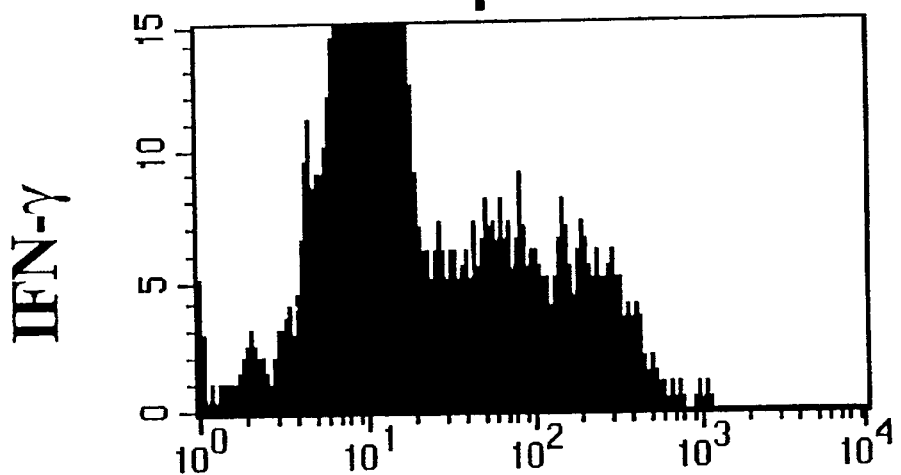
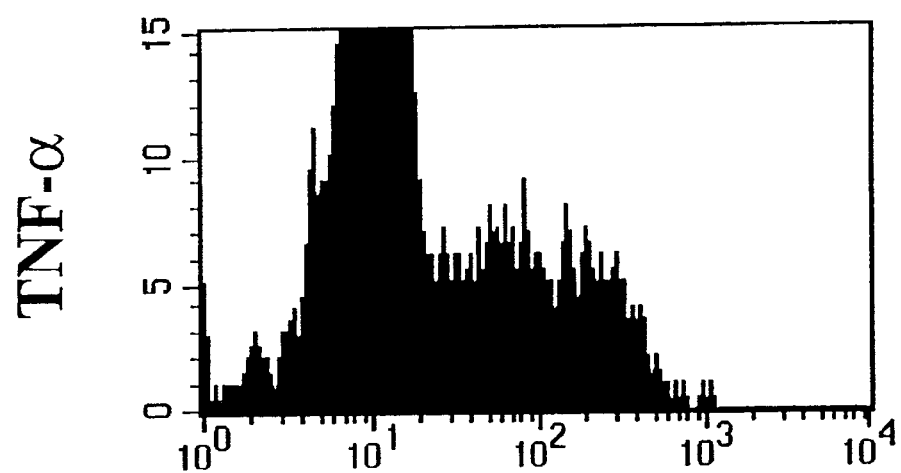
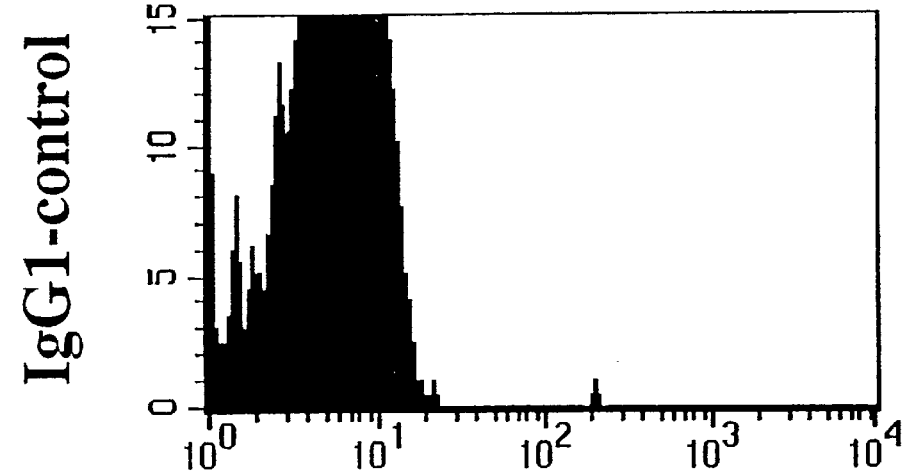

FIG. 16B  pt. H6.
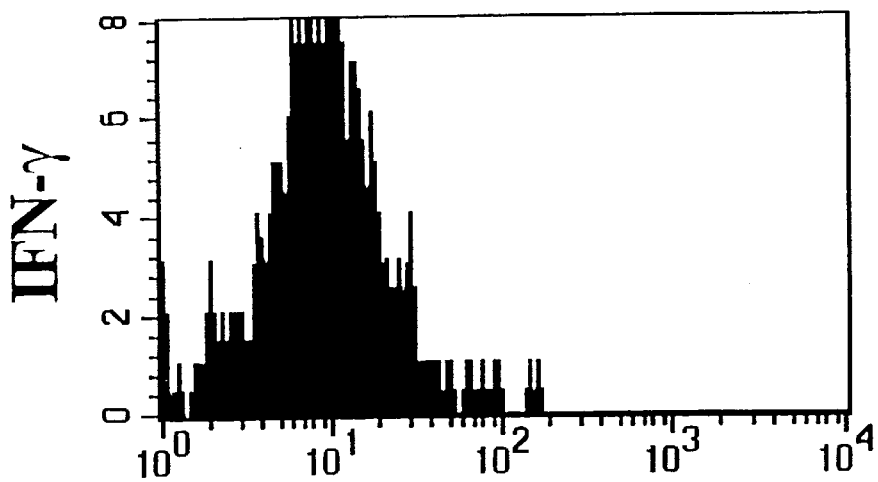
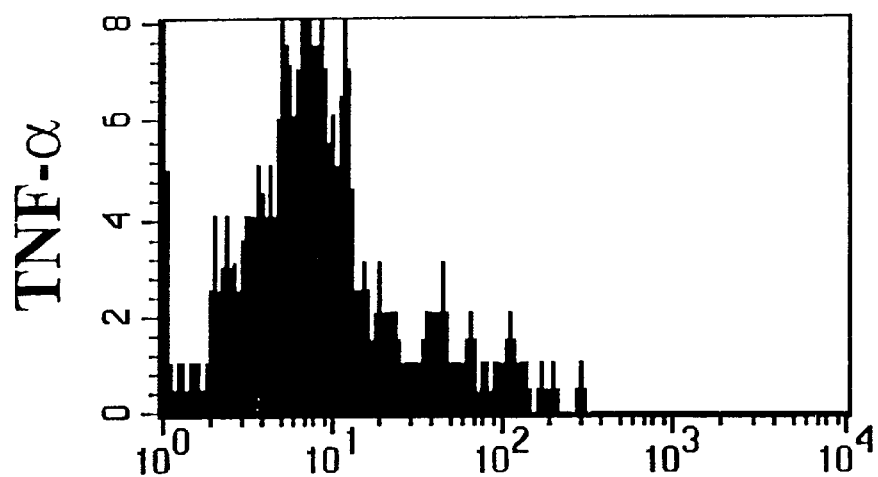
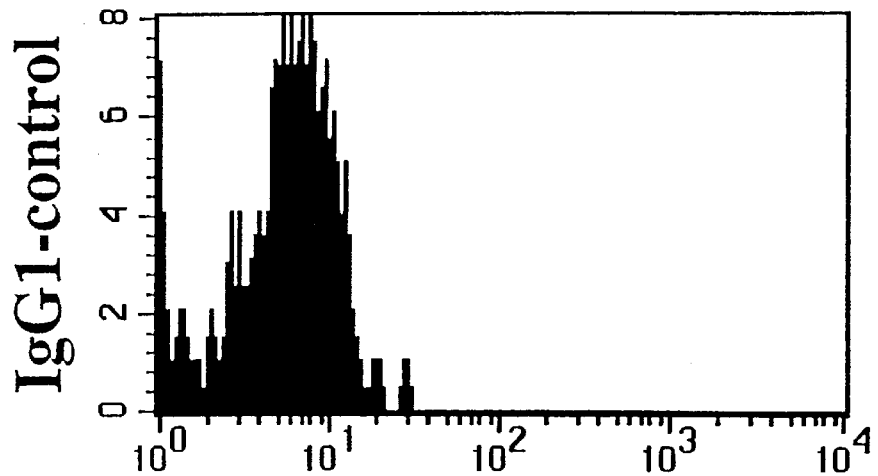

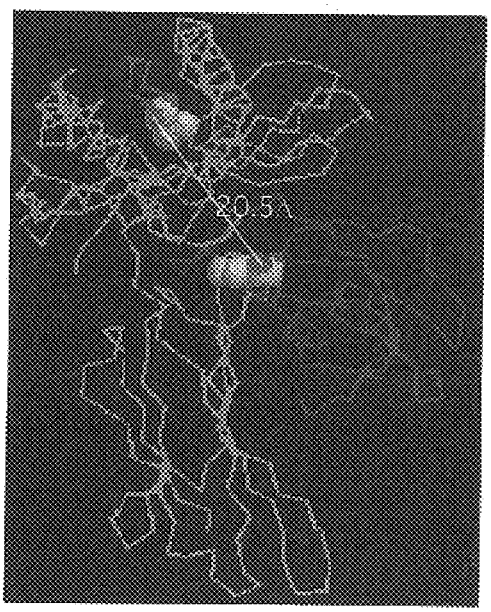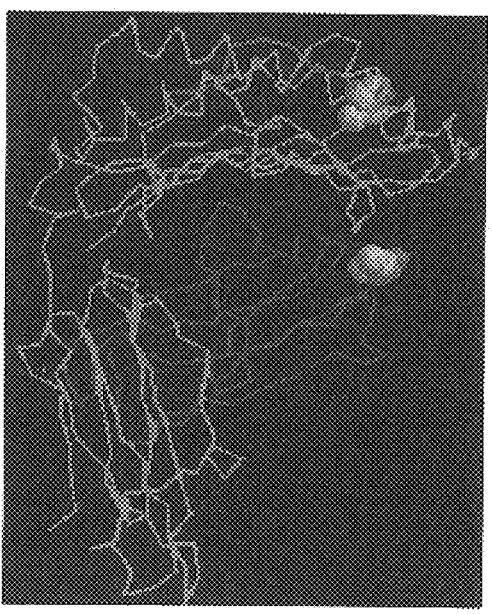
FIG. 18

SEQUENCE LISTING

<160> NUMBER OF SEQ ID NOS: 5

<210> SEQ ID NO 1
<211> LENGTH: 9
<212> TYPE: PRT
<213> ORGANISM: Human T-cell lymphotropic virus type 1

<400> SEQUENCE: 1

Leu Leu Phe Gly Tyr Pro Val Tyr Val
1               5

<210> SEQ ID NO 2
<211> LENGTH: 9
<212> TYPE: PRT
<213> ORGANISM: Influenza A virus

<400> SEQUENCE: 2

Gly Ile Leu Gly Phe Val Phe Thr Leu
1               5

<210> SEQ ID NO 3
<211> LENGTH: 9
<212> TYPE: PRT
<213> ORGANISM: Human immunodeficiency virus

<400> SEQUENCE: 3

Ser Leu Tyr Asn Thr Val Ala Thr Leu
1               5

<210> SEQ ID NO 4
<211> LENGTH: 28
<212> TYPE: DNA
<213> ORGANISM: Homo sapiens

<400> SEQUENCE: 4
gatacgcgtt gggctctcac tccatgag                                      28

<210> SEQ ID NO 5
<211> LENGTH: 36
<212> TYPE: DNA
<213> ORGANISM: Homo sapiens

<400> SEQUENCE: 5
cagtcgatgc ggccgcccat ctcagggtga ggggct                             36

USE OF MULTIVALENT CHIMERIC PEPTIDE-LOADED, MHC/IG MOLECULES TO DETECT, ACTIVATE OR SUPPRESS ANTIGEN-SPECIFIC T CELL-DEPENDENT IMMUNE RESPONSES

This application is a division of Ser. No. 09/150,622 filed Sep. 10, 1998 and claims the benefit of co-pending applications U.S. Ser. No. 60/058,573 filed Sep. 11, 1997 and U.S. Ser. No. 60/082,538 filed Apr. 21, 1998, which are incorporated by reference herein.

BACKGROUND OF THE INVENTION

The immune system is a defense system found in its most advanced form in higher vertebrates. This defense mechanism provides rapid and highly specific responses which are used to protect an organism against invasion by pathogenic microorganisms. It is the myriad of pathogenic microorganisms which have principally caused the evolution of the immune system to its current form. In addition to protection against infectious agents, specific immune responses are thought to be involved in surveillance against tumor development, the pathogenesis of autoimmune diseases, and transplant tissue rejection.

T cells are the major regulatory cells of the immune system. The regulatory functions of T cells depend not only on expression of a unique T cell receptor, but also on expression of a variety of accessory molecules and effector functions associated with an individual T cell response (i.e., a cytotoxic response versus a response characterized by secretion of effector molecules such as lymphokines). It is this regulatory function that often goes awry in the development of autoimmune diseases, plays a large role in tissue graft rejection, and can be important in tumor rejection.

Specificity of T cell responses is conferred by a unique set of cell surface receptors expressed on individual lymphocytes, called clonotypic T cell receptors (TCR). Cognate ligands of the clonotypic TCR are antigen major histocompatibility complex molecules (MHC). T cell receptors recognize antigens in the form of small antigenic peptides presented by MHC molecules on the surface of antigen presenting cells. While the interaction between an antigenic peptide and an MHC is quite stable, generally displaying a high affinity ($10^{-9}$ M) and consequent long half-life of dissociation, the interaction between a T cell receptor and a peptide/MHC complex—the critical recognition event in triggering T cells—is of relatively low affinity, between $10^{-4}$–$10^{-6}$ M. As a result of this low affinity, the T cell response is driven by the interaction of many T cell receptors on the surface of an individual T cell interacting with multiple antigenic peptide/MHC complexes on the surface of the antigen presenting cell.

Antigen-specific T cells play major roles in normal physiologic immune responses and in many disease states. Hyperactivation of antigen-specific T cells targeted toward self antigens is the underlying basis for the majority of autoimmune diseases, including multiple sclerosis, arthritis, and diabetes. Conversely, inactivity of tumor antigen-specific T cells allows tumors to grow. Thus, activation of dormant or tolerant tumor-specific T cells has been a major goal of cancer immunotherapy. Other important medical phenomena, such as rejection of transplanted organs, depend on the activity of T cells specific for alloantigens expressed by these organs. Antigen-specific suppression of undesired T cell responses could potentially eliminate organ graft rejection.

The use of soluble monovalent reagents to monitor and modulate antigen-specific T cells is limited by the fact that T cell receptors interact with peptide/MHC complexes with relatively low affinities (28–30). Thus, soluble monovalent analogs of either T cell receptors or peptide/MHC complexes do not effectively regulate immune responses.

Soluble multivalent analogs of proteins involved in immune responses have been made. Such analogs include CD4/Ig chimeras (41, 42), CR2/Ig chimeras (43), and class I MHC/Ig chimeras (20). The influence of valence on ligand affinity of these analogs is variable. For example, CD4/Ig molecules do not have a higher affinity for their ligand than soluble monovalent CD4 molecules. Tetravalent peptide/MHC complexes have high affinity for specific T cell receptors. However, divalent MHC analogs do not have a high enough affinity to allow staining or regulating antigen-specific T cells. Thus, there is a need in the art for agents which can specifically induce or suppress T cells specific for antigens associated with infections, allergies, tumors, transplanted organs, and autoimmune diseases.

SUMMARY OF THE INVENTION

It is an object of the invention to provide a set of reagents which specifically and stably bind to and modulate antigen-specific T cells. This and other objects of the invention are provided by one or more of the following embodiments.

One embodiment of the invention provides a composition comprising a chimeric protein. The chimeric protein comprises an MHC molecule and an immunoglobulin chain. The chimeric protein associates to form molecular complexes comprising at least two chimeric proteins per complex. An antigenic peptide is bound to each MHC molecule. Each MHC molecule within the molecular complex is bound to an identical antigenic peptide.

Still another embodiment of the invention provides a vector encoding a chimeric protein. The chimeric protein comprises an immunoglobulin heavy chain and an MHC molecule. The immunoglobulin is not IgG-1. The immunoglobulin heavy chain is C-terminal to the MHC molecule.

Even another embodiment of the invention provides a composition comprising a chimeric protein which comprises an MHC molecule and an Ig chain. The chimeric protein associates to form molecular complexes comprising at least two chimeric proteins per complex. The immunoglobulin chain is not an IgG heavy chain.

Another embodiment of the invention provides a composition comprising a cell in which a chimeric protein is bound to the surface of the cell. The chimeric protein comprises an MHC molecule and an immunoglobulin chain. The chimeric protein associates to form molecular complexes comprising at least two chimeric proteins per complex. An antigenic peptide is bound to each MHC molecule. Each MHC molecule within the molecular complex is bound to an identical antigenic peptide.

Still another embodiment of the invention provides a method for treating a patient suffering from an allergy. A chimeric protein which comprises an MHC molecule and an immunoglobulin chain is administered to a patient at a dose sufficient to suppress a T cell response associated with an allergy of the patient. The chimeric protein associates to form molecular complexes comprising at least two chimeric proteins per complex. An antigenic peptide is bound to each MHC molecule. Each MHC molecule within the molecular complex is bound to an identical antigenic peptide. The antigenic peptide is an antigen to which the patient has an allergic response.

Even another embodiment of the invention provides a method for treating a patient who has received or will receive an organ transplant. A chimeric protein which comprises an MHC molecule and an immunoglobulin chain is administered to the patient at a dose sufficient to suppress an immune response to the transplanted organ. The chimeric protein associates to form molecular complexes comprising at least two chimeric proteins per complex. An antigenic peptide is bound to each MHC molecule. Each MHC molecule within the molecular complex is bound to an identical antigenic peptide. The antigenic peptide is an alloantigen.

Another embodiment of the invention provides a method for treating a patient suffering from an autoimmune disease. A chimeric protein which comprises an MHC molecule and an immunoglobulin chain is administered to the patient at a dose sufficient to suppress an immune response associated with the autoimmune disease. The chimeric protein associates to form molecular complexes comprising at least two chimeric proteins per complex. An antigenic peptide is bound to each MHC molecule. Each MHC molecule within the molecular complex is bound to an identical antigenic peptide. The antigenic peptide is one to which the patient expresses an autoimmune response.

Still another embodiment of the invention provides a method for treating a patient having a tumor. A chimeric protein which comprises an MHC molecule and an immunoglobulin chain is administered to the patient at a dose sufficient to induce or enhance an immune response to the tumor. The chimeric protein associates to form molecular complexes comprising at least two chimeric proteins per complex. An antigenic peptide is bound to each MHC molecule. Each MHC molecule within the molecular complex is bound to an identical antigenic peptide. The antigenic peptide is a tumor-associated peptide.

Another embodiment of the invention provides a method for treating a patient having an infection. A chimeric protein which comprises an MHC molecule and an immunoglobulin chain is administered to the patient at a dose sufficient to induce or enhance an immune response to the infection. The chimeric protein associates to form molecular complexes comprising at least two chimeric proteins per complex. An antigenic peptide is bound to each MHC molecule. Each MHC molecule within the molecular complex is bound to an identical antigenic peptide. The antigenic peptide is an infectious agent-associated peptide.

Even another embodiment of the invention provides a method of labeling antigen-specific T cells. A sample comprising antigen-specific T cells is contacted with a chimeric protein. The chimeric protein comprises an MHC molecule and an immunoglobulin chain. The chimeric protein associates to form molecular complexes comprising at least two chimeric proteins per complex. Each MHC molecule within the molecular complex is bound to an identical antigenic peptide. The antigenic peptide specifically binds to and labels the antigen-specific T cells.

These and other embodiments of the invention provide the art with tools and methods for modulating antigen-specific T cell immune responses.

BRIEF DESCRIPTION OF THE DRAWINGS

The file of this patent contains at least one drawing executed in color. Copies of this patent with color drawings are provided to the Patent and Trademark Office with payment of the necessary fee.

FIG. 1.

FIG. 2. Peptide loaded $L^d$/Ig molecules specifically bind to T cells expressing their cognate ligand. $L^d$/Ig molecules were loaded with peptides (100 $\mu$M) overnight. Peptides used included the 2C CTL reactive peptide p2Ca, a tumor peptide specific for murine CT 26 cells, AH1, and another $L^d$-restricted model tumor antigen derived from β-galactosidase, β-gal. After overnight incubation, peptide/$L^d$/Ig complexes were used to stain the antigen-specific T cells 2C and anti-CT 26 CTL. Viable T cells were purified using lymphocyte-M separation and reacted with 20 $\mu$g/ml of the peptide/$L^d$/Ig complex for 1 hour at RT. Cells were than washed and stained with goat anti-mouse PE and analyzed by flow cytometry. Representative histograms are shown. FIG. 2B. CT 26 specific T cells were only reactive with $^{AH1}L^d$/Ig but not with either $^{p2Ca}L^d$/Ig or $^{β-gal}L^d$/Ig complexes.

FIG. 3. Schematic of $K^b$/IgG loading scheme.

FIG. 10. $^{pep}$MHC/Ig complexes specifically inhibit proliferation of 2C CTL by allogeneic target cells. 2C T cells were incubated with various concentrations of $^{SIY}$K$^b$/Ig for 2.5 hours at 37° C. Irradiated (3000 rads) freshly isolated BALB/c splenocytes (expressing H-2 L$^d$) were added to the responders cells ligands at 2.5×10$^5$/well. Following a 60 h incubation, cells were pulsed with [$^3$H]thymidine and incubated for an additional 18 h before being harvested and counted.

FIG. 11. Peptide loaded HLA-A2/Ig specifically stains HTLV-1 Tax11–19 or HIV p17 Gag77–85-specific T cell clones.

FIG. 14. HTLV-1 Tax11–19 specific CD8$^+$ T cells accumulate in cerebrospinal fluid. Cerebrospinal fluid and peripheral blood were obtained from an HAM/TSP patient (H1) the same day and analyzed using Tax-A2/Ig. 9×10$^4$ cells were obtained from cerebrospinal fluid and stained using Tax/A2-Ig and Gag/A2-Ig together with mouse anti-human CD8-FITC, as described in FIG. 13. Freshly obtained, Ficoll purified PBL were analyzed in parallel. FIG. 14B. CD4/CD8 analysis showed that the ratio of CD4/CD8 was 1.1 in the CSF and 1.5 in the PBL, due to a higher number of CD8$^+$ T cells in CSF.

FIG. 15. Tax-specific CD8$^+$ cells from HAM/TSP patients express the cell surface activation marker HLA-DR. Using three-color flow cytometry, Tax-specific CD8$^+$ cells were gated and analyzed for HLA-DR expression using mouse anti-human HLA-DR-FITC (solid line) and an isotype matched irrelevant mouse IgG2a-FITC control (dotted line). FIGS. 15A and 15B. In 2 different symptomatic HAM/TSP patients, 41–50% of the Tax-specific CD8$^+$ T cells stained positive for HLA-DR expression. FIG. 15C. In contrast, only 21% of the Tax-specific CD8$^+$ T cells from patient H6, who has a very mild form of the disease, stained positive. FIG. 15D shows a non-stimulated staining control. FIG. 15E shows control staining from PHA-stimulated CD8$^+$ PBL from a healthy donor.

FIG. 16. Tax-specific CD8$^+$ cells from HAM/TSP patients express intracellular IFN-γ and TNF-α. Using three-color flow cytometry, Tax-specific CD8$^+$ cells were gated and analyzed for intracellular cytokine expression. FIG. 16A. Using mouse anti-human IFN-γ-PE, mouse anti-human TNF-α-PE, and an isotype matched irrelevant mouse IgG1-PE control, 28% of the Tax-specific CD8$^+$ cells from H1 expressed intracellular IFN-γ, and 29% expressed TNFα. FIG. 16B. Only 8% of the Tax-specific CD8$^+$ cells from H6 expressed intracellular IFN-γ and TNF-α.

FIG. 18. Structure of HLA-A2 complexed with Tax 11–19 peptide. Two views of the 3-D structure of HLA-A2 heavy chain (green), β2M (purple) and tax 11–19 antigenic peptide (red) are shown. The carboxyl terminal, position 9, of tax 11–19 peptide and amino terminal position 1 of the β2M polypeptides are represented as space filling diagrams while the rest of the chains are shown as ribbon diagrams. Oxygen groups in the space filled amino acid residues are represented as red balls while the nitrogen groups are seen as light blue ones. The distance between the amino terminus of the β2M molecule and position 9 of the peptide was found to be 20.49 Angstroms. Open access of the region between the ends of the peptide and β2M molecule can be seen best on the side view of the complex (left-hand side of FIG. 18). the peptide for the class I complex secondary to modification of the carboxyl terminal tax peptide, position 9. Anchoring of the peptide to the MHC molecule is achieved in part through bonds to the carboxylterminal oxygen that will be unavailable in the tethered peptide-β2M complex. This decreased affinity may be compensated for by stabilization with β2M.

DETAILED DESCRIPTION OF THE INVENTION

The invention provides soluble, high affinity, multivalent analogs of MHC molecules. These reagents can be used diagnostically, to detect antigen-specific T cells, or for therapy, either to activate or suppress antigen-specific T cells in vitro and in vivo. Therefore, these reagents can be used in selective immune-based therapy of infections, allergies, autoimmune diseases, cancer, and organ transplant rejection.

The reagents of the invention express a single peptide/MHC complex in a multivalent array. The multivalent array is formed using an immunoglobulin backbone as a molecular scaffold for presentation of an antigenic peptide/class I complex. These arrays can be made by producing chimeric genes in which an MHC gene is linked to the 5' end of an immunoglobulin heavy chain, as described below. When these constructs are expressed, for example, in baculovirus or hybridoma cells, they produce chimeric molecules which are multivalent, based on the valence of the molecular scaffold, the immunoglobulin molecule.

Figure 1A:
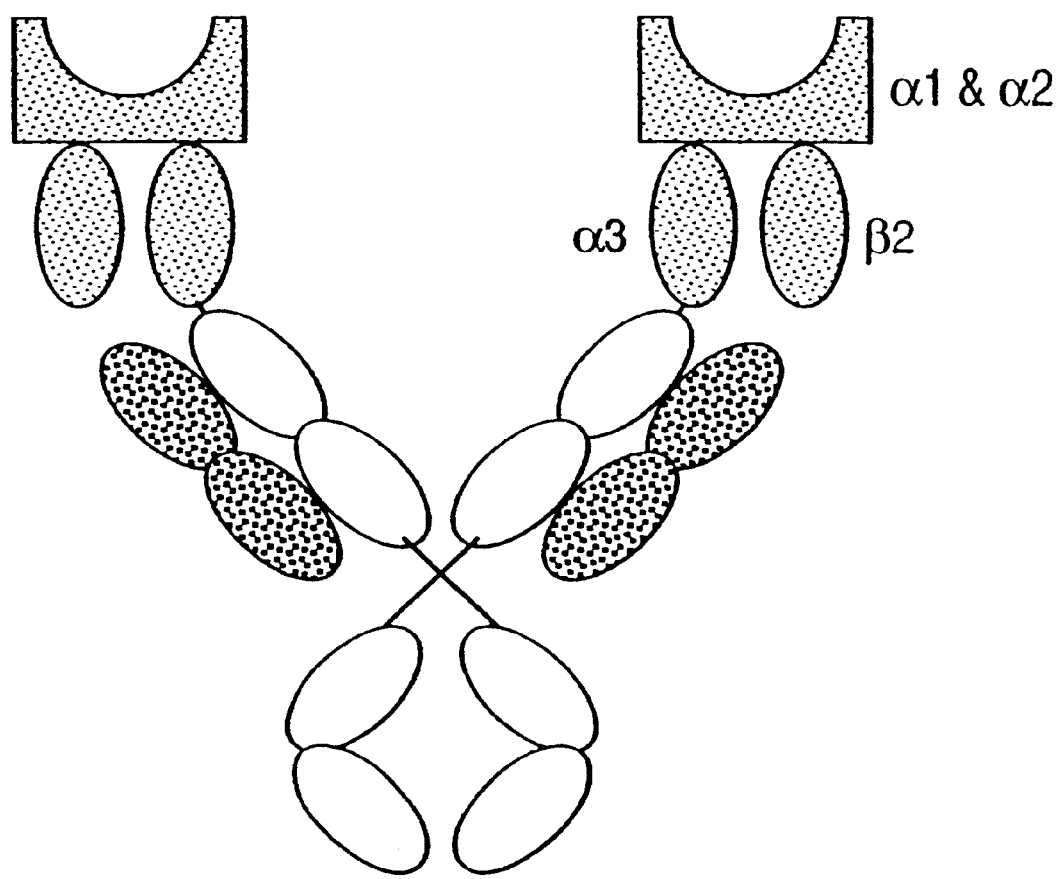
FIG. 1A, schematic of chimeric MHC/Ig molecules formed in a conformationally intact fashion at the ends of the immunoglobulin heavy chains.
Figure 1B:
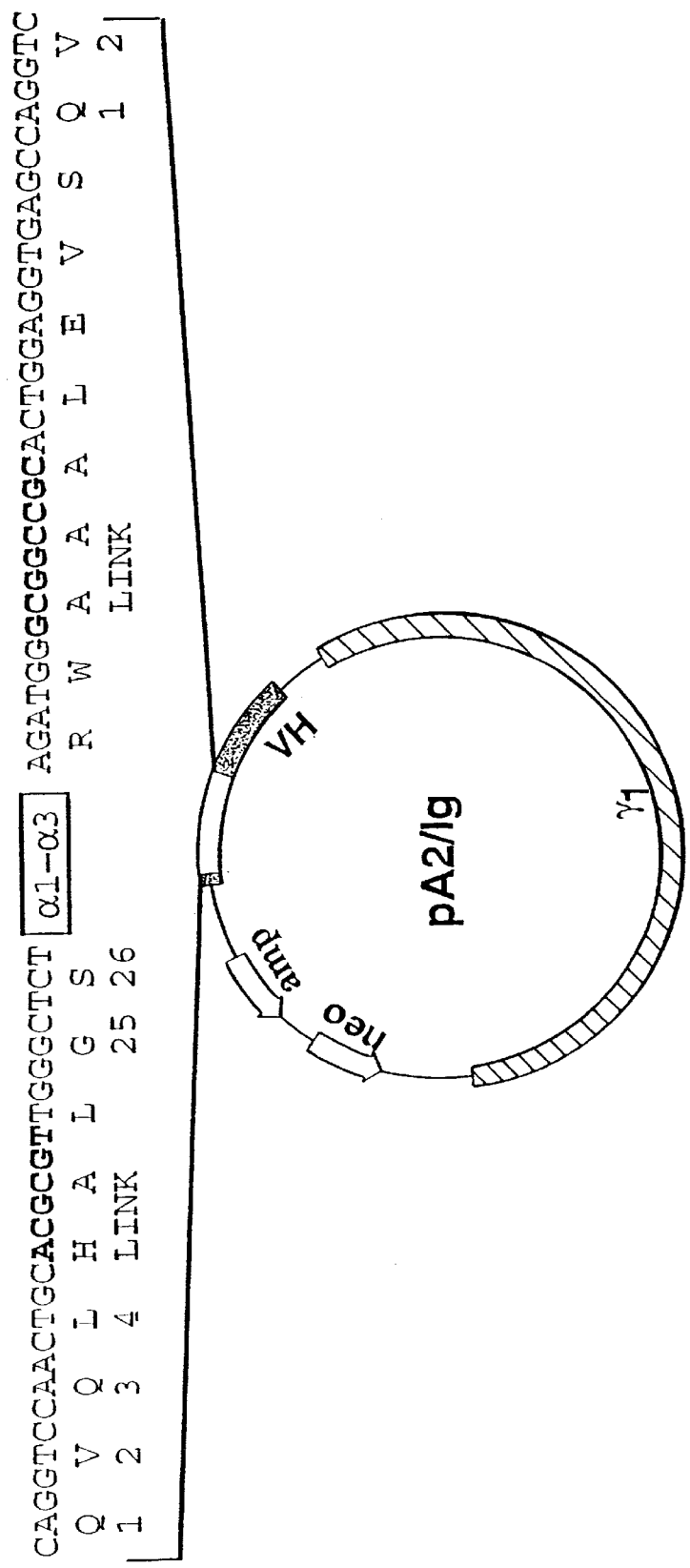
FIG. 1B, schematic of the pA2/Ig plasmid containing the regions encoding the extracellular domains ($\alpha 1$–$\alpha 3$) of the HLA-A2 class I MHC molecule genetically linked to the variable region of an IgG1 heavy chain gene.

The chimeric MHC/Ig molecules are formed in a conformationally intact fashion at the ends of the immunoglobulin heavy chains (see FIG. 1A for a schematic representation). When homogeneously loaded with antigenic peptides, MHC/Ig chimeras ($^{pep}$MHC/Ig molecules) have sufficiently high affinity to produce stable binding and can modulate antigen-specific T cells.

These constructs have a number of other useful features. For example, they are extremely stable and easy to produce, based on the stability and secretion efficiency provided by the immunoglobulin backbone. Further, by altering the Fc portion of the immunoglobulin, different biological functions can be provided to the molecule based on biological functions afforded by the Fc portion. Substitution of the Fc portion of one type of immunoglobulin gene for another is within the skill of the art.

This class of reagents represents a new tool for understanding a variety of immunologic diseases. The observation that a divalent MHC/Ig chimeric protein stably binds to its cognate T cell receptor is surprising since the monovalent peptide-MHC complex dissociates rapidly from complexes with TCR with a half life of less than 1 minute (27) and the affinity of the T cell receptor for peptide-MHC complexes is relatively low (~$10^{-5}$ μM) (28–30). Stable binding of the dimeric HLA-A2/Ig complex to cognate T cells is likely based on two features related to the immunoglobulin scaffold. First, the multivalent nature of the complex provides an increase in avidity. Second, the unique flexibility of the immunoglobulin hinge region likely promotes maximal avidity enhancement with our divalent construct.

Chimeric proteins of the invention comprise an immunoglobulin heavy chain and an MHC molecule. The immunoglobulin heavy chain can be the heavy chain of an IgM, IgD, IgG1, IgG3, IgG2β, IgG2α, IgE, or IgA. Preferably, an IgG heavy chain is used to form divalent chimeric proteins of the invention. If multivalent chimeric proteins are desired, IgM or IgA heavy chains can be used to provide pentavalent or tetravalent chimeras, respectively. Chimeric proteins with other valencies can also be constructed, using multiple immunoglobulin heavy chains.

The immunoglobulin heavy chain is fused to a polypeptide chain of an MHC molecule. Methods of making fusion proteins, either recombinantly or by covalently linking two protein segments, are well known. Preferably, fusion proteins are expressed recombinantly, as products of expression constructs. Expression constructs of the invention comprise a polynucleotide or vector which encodes a fusion protein of the invention in which an immunoglobulin heavy chain is C-terminal to an MHC molecule.

Expression vectors of the invention can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

Host cells comprising expression vectors of the invention can be prokaryotic or eukaryotic. Bacterial systems for expressing fusion proteins of the invention include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad. Sci. USA* (1983) 80: 21–25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202: 302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376, U.S. Pat. No. 4,837,148, U.S. Pat. No. 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 26: 205–221, Yelton et al., *Proc. Natl. Acad. Sci. USA* (1984) 81: 1470–1474, Kelly and Hynes, *EMBO J.* (1985) 4: 475479; EP 244,234, and WO 91/00357.

Expression of fusion proteins of the invention in insects can be carried out as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl. Acad. Sci. USA* (1985) 82: 8404, Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47–55, Miller et al., in GENETIC ENGINEERING (Setlow, J. K. et al. eds.), Vol. 8 (Plenum Publishing, 1986), pp. 277–279, and Maeda et al., *Nature*, (1985) 315: 592–594.

Expression of fusion proteins of the invention in mammalian cells can be achieved as described in Dijkema et al., *EMBO J.* (1985) 4: 761, Gorman et al, *Proc. Natl. Acad. Sci. USA* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44, Barnes and Sato, *Anal. Biochem.* (1980) 102: 255, U.S. Pat. Nos. 4,767,704, 4,657,866, 4,927,762, 4,560,655, WO 90/103430, WO 87/00195, and U.S. Pat. No. RE 30,985.

Each MHC molecule within a molecular complex is bound to an identical antigenic peptide. Any peptide capable of inducing an immune response can be bound to the MHC molecule, including peptides which cause allergic or autoimmune responses, alloantigens, tumor-associated peptides, and peptides of infectious agents, such as bacteria, viruses, or fungi.

Antigenic peptides can be bound to the antigen binding site of the MHC molecule or to the amino-terminus of either an MHC class II β chain or a $\beta_2$ microglobulin. Binding, or "loading" of the antigenic peptide to the chimeric protein can be carried out actively or passively, as described in Example 2, below. The antigenic peptide can be covalently bound to the chimeric protein.

Optionally, a peptide tether can be used to link an antigenic peptide to $\beta_2$ microglobulin. Crystallographic analyses of multiple class I MHC molecules indicate that the amino terminus of β2M is very close, approximately 20.5 Å away, from the carboxyl terminus of the antigenic peptide resident in the MHC peptide binding groove (see FIG. 18). Thus, using a relatively short linker sequence, approximately 13 amino acids in length, one can tether a peptide to the amino terminus of β2M. If the sequence is appropriate, that peptide will bind to the MHC binding groove (see Example 17, below).

Molecular complexes of the invention can be used diagnostically, to label antigen-specific cells in vitro or in vivo. A sample comprising antigen-specific T cells can be contacted with a molecular complex in which each MHC molecule is bound to an identical antigenic peptide. The sample can be, for example, peripheral blood, lymphatic fluid, lymph nodes, spleen, thymus, or bone marrow.

The antigenic peptide specifically binds to the antigen-specific T cells and labels them with the antigenic peptide-loaded complex. Antigenic peptide/MHC complexes can be, but need not be, conjugated to a reporter group, such as a radiolabel or fluorescent label, to facilitate detection. The molecular complex can be in solution or can be affixed to a solid substrate, such as a glass or plastic slide or tissue culture plate or latex, polyvinylchloride, or polystyrene beads.

Antigen-specific T cells which are bound to the antigenic peptides can be separated from cells which are not bound. Any method known in the art can be used to achieve this separation, including plasmapheresis, flow cytometry, or differential centrifugation. Antigen-specific T cells which have been isolated from a patient can be treated with a reagent, such as a cytokine, a chemotherapeutic agent, or an antibody, and reinfused into the patient to provide a therapeutic effect. Optionally, the number of antigen-specific T cells which are bound to the antigenic peptides can be quantitated or counted, for example by flow cytometry.

Molecular complexes of the invention can also be used to activate or inhibit antigen-specific T cells. It is possible to conjugate toxin molecules, such as ricin or Pseudomonas toxin, to molecular complexes of the invention. Similarly, molecular complexes can be conjugated to molecules which stimulate an immune response, such as lymphokines or other effector molecules. Doses of the molecular complex can be modified to either activate or inhibit antigen-specific T cells.

A sample which comprises antigen-specific T cells can be contacted, in vivo or in vitro, with molecular complexes in which each MHC molecule is bound to an antigenic peptide. The antigenic peptide specifically binds to and activates or inhibits the antigen-specific T cells. For example, cytokine release from specific T cell subsets can be stimulated or suppressed. Hewitt et al., *J. Exp. Med.* 175:1493 (1992); Choi et al., *Proc. Natl. Acad. Sci.* 86:8941 (1989); Kappler et al., *Science* 244:811 (1989); Minasi et al., *J. Exp. Med.* 177:1451 (1993); Sundstedt et al., *Immunology* 82:117 (1994); and White et al., *Cell* 56:27 (1989).

Molecular complexes of the invention can be used therapeutically, to inhibit or stimulate immune responses. For example, molecular complexes comprising antigenic peptides to which a patient has an allergic response can be administered to the patient in order to treat an allergy. The molecular complexes are administered to the patient at a dose sufficient to suppress or reduce a T cell response associated with the allergy.

Similarly, a patient who has received or will receive an organ transplant can be treated with molecular complexes of the invention. Molecular complexes in which each ligand binding site is bound to an alloantigen can be administered to a patient at a dose sufficient to suppress or reduce an immune response to the organ transplant. Alloantigens include the HLA antigens, including class I and class II MHC molecules, and minor histocompatibility antigens such as the ABO blood group antigens, autoantigens on T and B cells, and monocyte/endothelial cell antigens.

Autoimmune diseases, such as Goodpasture's syndrome, multiple sclerosis, Graves' disease, myasthenia gravis, systemic lupus erythematosus, insulin-dependent diabetes melitus, rheumatoid arthritis, pemphigus vulgaris, Addison's disease, dermatitis herpetiformis, celiac disease, and Hashimoto's thyroiditis, can be similarly treated. A patient who suffers from an autoimmune disease can be treated with molecular complexes of the invention in which each ligand binding site is bound to an antigenic peptide to which the patient expresses an autoimmune response. The molecular complexes are administered to the patient at a dose sufficient to suppress or reduce the autoimmune response.

Immune responses of a patient can also be induced or enhanced using molecular complexes of the invention. Molecular complexes in which each ligand binding site is bound to a peptide expressed by a tumor can be used to treat the tumor. The peptide can be a tumor-specific peptide, such as EGFRvIII, Ras, or p185$^{HER2}$, or can be a peptide which is expressed both by the tumor and by the corresponding normal tissue. Similarly, molecular complexes in which each ligand binding site is bound to a peptide of an infectious agent, such as a protein of a bacterium or virus, can be used to treat infections. In each case, the appropriate molecular complexes are administered to the patient at a dose sufficient to induce or enhance an immune response to the tumor or the infection.

Molecular complexes of the invention can be bound to the surface of a cell, such as a dendritic cell. A population of molecular complexes in which all ligand binding sites are bound to identical antigenic peptides can also be bound to the cell. Binding can be accomplished by providing the fusion protein of the molecular complex with an amino acid sequence which will anchor it to the cell membrane and expressing the fusion protein in the cell or can be accomplished chemically, as is known in the art.

Compositions comprising molecular complexes of the invention can comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Compositions of the invention can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a composition of the invention.

The particular dosages of divalent and multivalent molecular complexes employed for a particular method of treatment will vary according to the condition being treated, the binding affinity of the particular reagent for its target, the extent of disease progression, etc. However, the dosage of molecular complexes will generally fall in the range of 1 pg/kg to 100 mg/kg of body weight per day. Where the active ingredient of the pharmaceutical composition is a polynucleotide encoding fusion proteins of a molecular complex, dosage will generally range from 1 nM to 50 $\mu$M per kg of body weight.

The amounts of each active agent included in the compositions employed in the examples described herein provide general guidance of the range of each component to be utilized by the practitioner upon optimizing the method of the present invention for practice either in vitro or in vivo. Moreover, such ranges by no means preclude use of a higher or lower amount of a component, as might be warranted in a particular application. For example, the actual dose and schedule may vary depending on whether the compositions are administered in combination with other pharmaceutical compositions, or depending on individual differences in pharmacokinetics, drug disposition, and metabolism. Similarly, amounts may vary for in vitro applications depending on the particular cell line utilized, e.g., the ability of the plasmid employed to replicate in that cell line. For example, the amount of nucleic acid to be added per cell or treatment will likely vary with the length and stability of the nucleic acid, as well as the nature of the sequence, and may be altered due to factors not inherent to the method of the present invention, e.g., the cost associated with synthesis, for instance. One skilled in the art can easily make any necessary adjustments in accordance with the necessities of the particular situation.

A sufficient dose of the composition for a particular use is that which will produce the desired effect in a host. This effect can be monitored using several end-points known to those skilled in the art. For example, one desired effect might comprise effective nucleic acid transfer to a host cell. Such transfer could be monitored in terms of a therapeutic effect, e.g., alleviation of some symptom associated with the disease being treated, or further evidence of the transferred gene or expression of the gene within the host, e.g, using PCR, Northern or Southern hybridization techniques, or transcription assays to detect the nucleic acid in host cells, or using immunoblot analysis, antibody-mediated detection, or the assays described in the examples below, to detect protein or polypeptide encoded by the transferred nucleic acid, or impacted level or function due to such transfer.

The examples describe the use of chimeric molecules of the invention when loaded with antigenic peptides in the detection and regulation of antigen-specific T cell responses. In these examples, MHC class I molecules are used to target CD8 cells. However, MHC class II/Ig chimeras can also be produced by linking the $\alpha$ and $\beta$ chains of MHC class II molecules to the ends of the heavy and light chains of the immunoglobulin, respectively.

Quantitation of HTLV-1 Tax11–19-specific T cells in peripheral blood with peptide-loaded HLA-A2/Ig demonstrates that previous precursor frequency analysis of Tax-specific, $CD8^+$, CTL by LDA may have significantly underestimated the actual number of Tax-specific T cells (12). Using reagents of the invention, we were able to show that the number of Tax-specific $CD8^+$ T cells assessed by Tax-A2/Ig staining was roughly 10 to 30 fold higher than previously estimated by LDA (12). The accuracy of LDA is probably compromised by the fact that it depends on the ability to expand individual cells in vitro to numbers large enough to be detected by functional tests such as chromium release. (31–34). The frequencies determined by direct staining with Tax-A2/Ig are not due to non-specific binding. Tax-A2/Ig positively staining $CD8^+$ cells were virtually undetectable in $HTLV-1^-$ individuals, in $HLA-A2^-$ patients with HAM/TSP and in control HLA-A2 patient infected with a different retrovirus, HIV, where a significant number of cells were specific for p17 Gag 77–85 when stained with p17 Gag 77–85 loaded A2/Ig.

In addition to using peptide-loaded HLA-A2/Ig to analyze antigen-specific T cell populations, the immunoglobulin scaffold of the HLA-A2 Ig chimera provides a variety of other options, including targeting of antigen-specific T cells in vivo. The diversity of in vivo biological effects mediated by the different Fc regions which can be inserted onto this molecule allow for its application in targeting antigen-specific T cells in vivo, either for amplification of antigen-specific T cells as a vaccine or for elimination of pathogenic T cells in diseases such HAM/TSP as well as classical autoimmune diseases.

The high number of HTLV-1 Tax11–19-specific $CD8^+$ T cells in $HLA-A2^+$ HAM/TSP patients suggests the HTLV-1 Tax11–19 may represent the immunodominant epitope in this pathogenic immune response. Thus, soluble divalent MHC/Ig can also have therapeutic application in targeting and eliminating HTLV-1-specific $CD8^+$ T lymphocytes in HAM/TSP.

In the examples presented below the molecules are divalent, based on a molecular scaffold using an IgG molecule, but could also be made multivalent using an IgM for the immunoglobulin portion or using other immunoglobulin molecules as a backbone. The same genetic constructs can be used, substituting known genes encoding other Ig molecules for the IgG-1 exemplified below. Such substitution is well within the skill of the art.

The examples are provided for exemplification purposes only and are not intended to limit the scope of the invention described in broad terms above.

EXAMPLE 1

This example demonstrates staining of antigen-specific T cells by peptide loaded MHC/Ig chimeras.

The increased affinity of peptide-loaded MHC/Ig molecules allows for stable binding to cognate T cells (FIG. 2).

Figure 2A:
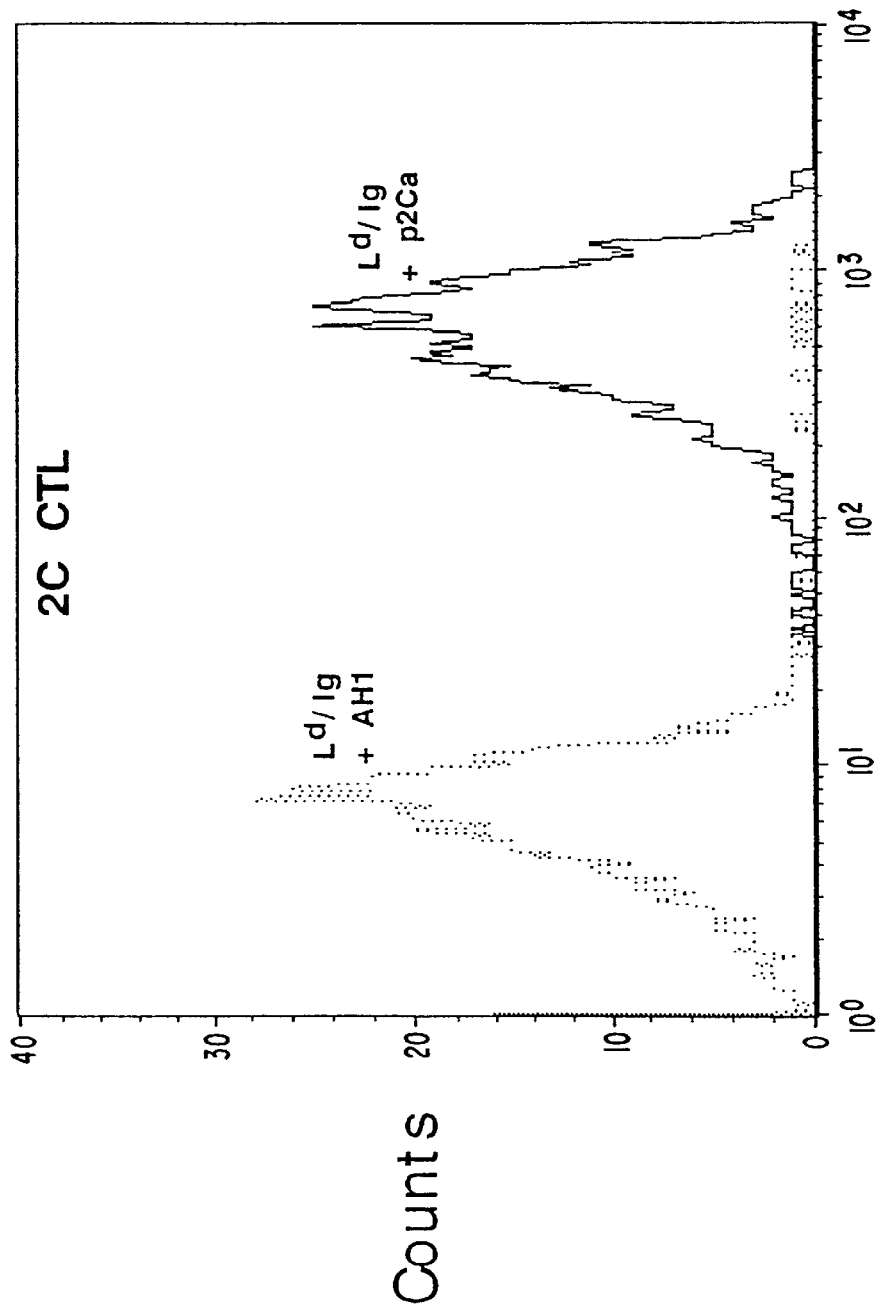
FIG. 2A. 2C CTL were reactive with $^{p2Ca}L^d$/Ig complexes but not with $^{AH1}L^d$/Ig complexes.
Figure 4:
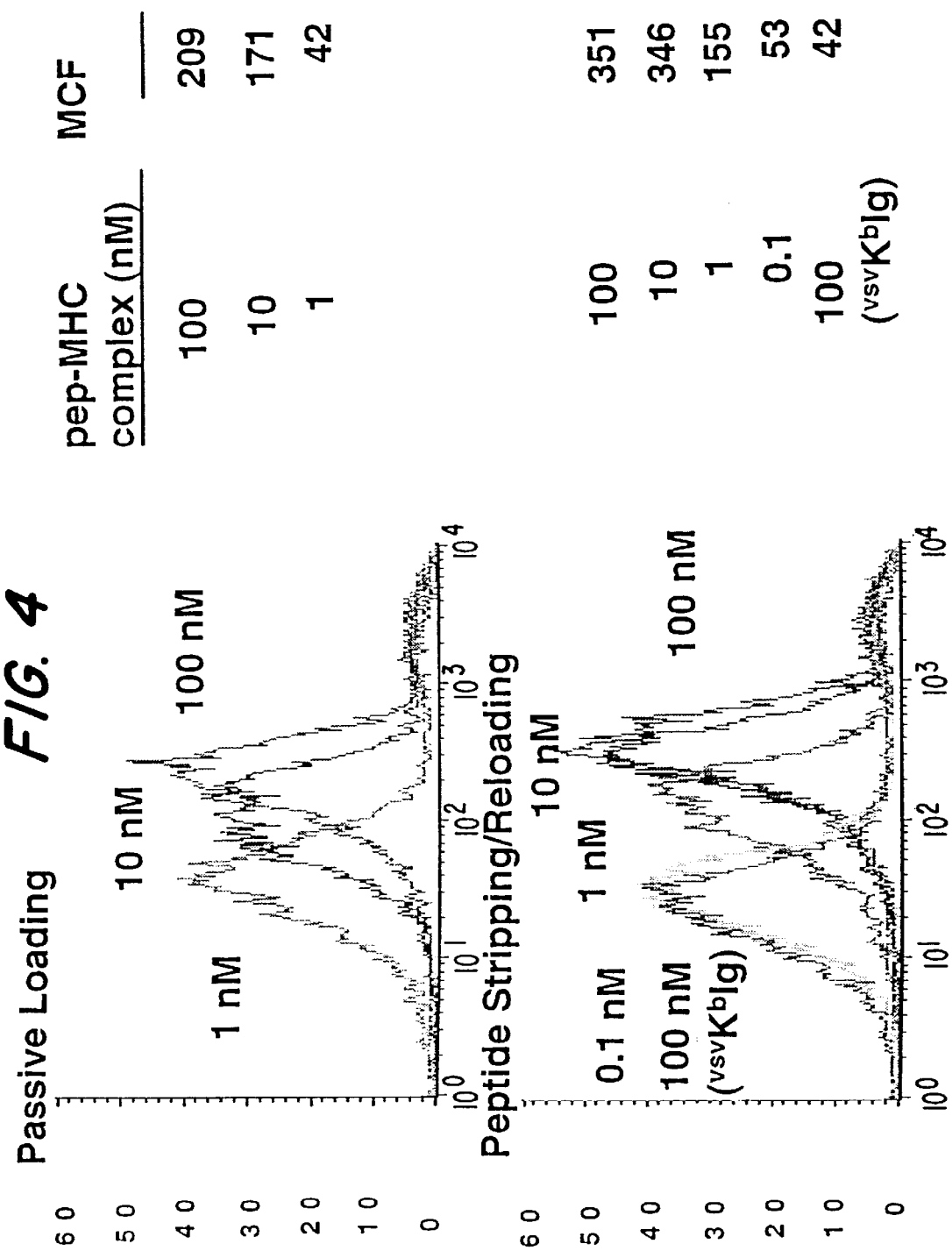
FIG. 4. Peptide stripping and reloading enhances effective peptide loading of $K^b$/Ig molecules. $K^b$/Ig molecules were either "passively" or "actively" loaded with peptides (100 $\mu$M) as described. Peptides used included the 2C CTL reactive peptide SIY. A control peptide included another $K^b$-binding peptide, VSV. Varying dilutions of $^{pep}$MHC/Ig complexes were used to stain 2C specific T cells. Viable T cells were purified using lymphocyte-M separation and reacted with 20 $\mu$g/ml of the peptide/$L^d$/Ig complex for 1 hour at 4° C. Cells were than washed and stained with goat anti-mouse PE and analyzed by flow cytometry. Representative histograms are shown. are shown.
Figure 5:
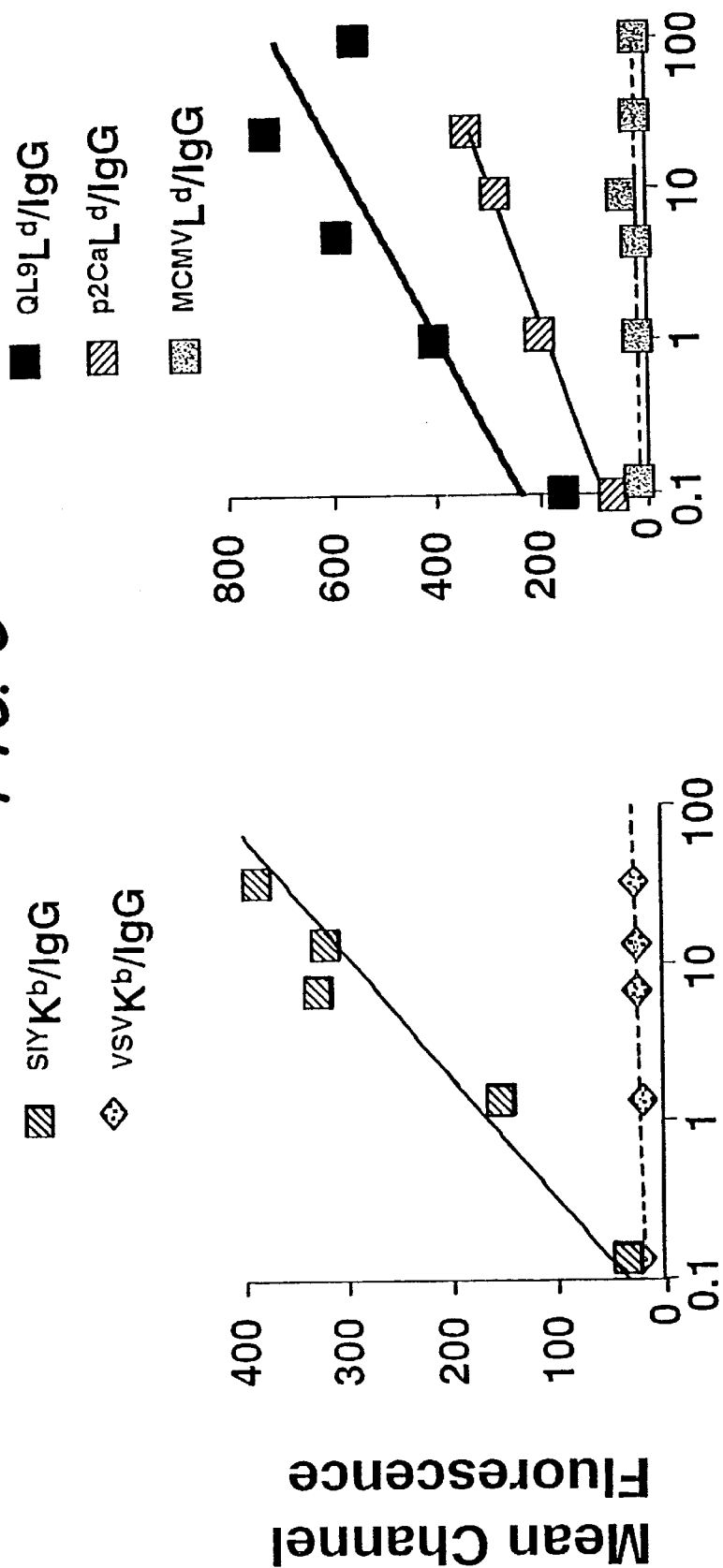
FIG. 5. Peptide loaded MHC/Ig molecules bind T cells with high affinity. $L^d$/Ig or $K^b$/Ig molecules were loaded with peptides (100 $\mu$M) as described. Peptides used included the 2C CTL reactive H-2$L^d$-restricted peptides QL9, and p2Ca, and the 2C CTL reactive H-2$k^b$ restricted peptide SIY. Control peptides included another $L^d$-binding peptide MCMV and a $K^b$-binding peptide VSV. Varying concentration of peptide/MHC/Ig complexes were used to stain 2C specific T cells as previously described. Representative histograms were analyzed and the data are presented as mean channel fluorescence values.

Antigen-specific T cells are specifically stained with MHC class I/IgG reagents loaded with the defined antigenic peptides. Using soluble divalent murine class I, H-2 $L^d$/Ig loaded with either p2Ca, a peptide reactive with 2C cytotoxic T lymphocytes (CTL), or AH-1, a peptide-specific for a tumor CTL line that recognizes the murine tumor CT26, one can label antigen-specific CTL. As shown in FIG. 2A, 2C CTL were reactive with $^{p2Ca}L^d$/Ig complexes but not with $^{AH1}L^d$/Ig complexes. CT 26 specific T cells were only reactive with $^{AH1}L^d$/Ig but not with either $^{p2Ca}L^d$/Ig (not shown) or $^{\beta\text{-}gal}L^d$/Ig complexes (FIG. 2B). In contrast to these results, tetravalent peptide/MHC complexes were previously found to be required for staining when the MHC was coordinated around avidin.

EXAMPLE 2

This example demonstrates passive versus active loading of the chimeras.

A critical feature of these chimeric compounds is the ability to load each of the MHC portions with a single well-defined peptide representing the peptide antigen of interest. To effectively study the influence of divalent MHC on antigen-specific responses, parameters for peptide reconstitution of divalent MHC molecules were established. These parameters vary between the different MHC/Ig chimeras.

A variety of different approaches were analyzed to optimize peptide loading of the chimeric MHC/Ig molecules. Optimal loading of H-2 $K^b$/Ig was found to entail alkaline stripping, rapid neutralization, and slow refolding (see FIG. 3 for a schematic). This protocol is referred to herein as "actively" loading $^{pep}$MHC/Ig complexes. "Passively" loading $^{pep}$MHC/Ig complexes is accomplished simply by incubating peptides of interest with the MHC/Ig complex over 48 hours.

When tested as reagents for staining specific T cells, "actively" loaded $^{SIY}K^b$/Ig molecules were significantly better than "passively" loaded $^{SIY}K^b$/Ig. Staining of antigen-specific T cells was seen at concentrations as low as 0.1 nM with "actively" loaded $^{SIY}K^b$/Ig, mean channel fluorescence (MCF) of cells stained with 0.1 nM of an "actively" loaded $^{SIY}K^b$/Ig was 53, compared to MCF of 42 for $K^b$/Ig that was "actively" loaded with a control peptide, VSV.

Staining of antigen-specific T cells required approximately 10 nM of "passively" loaded $^{SIY}K^b$/Ig. Half maximal staining of antigen-specific 2C T cells was seen with 1 nM of "actively" loaded $^{SIY}K^b$/Ig, but required approximately 10 nM of "passively" loaded $^{SIY}K^b$/Ig. Thus, the "actively" loaded $^{pep}K^b$/Ig complexes are approximately 10–100 fold more effective than "passively" loaded $^{pep}$MHC/Ig complex in staining peptide specific T cells.

EXAMPLE 3

This example demonstrates the sensitivity of $^{pep}$MHC/Ig complexes.

The utility of these reagents is not indicated solely by their specificity but also their sensitivity. Low concentrations of $^{pep}$MHC/Ig complexes detect antigen-specific T cells. Nanomolar concentrations of peptide-loaded MHC/Ig complexes can be used to stain 2C T cells. When analyzed with either $^{Q19}L^d$/Ig or $^{SIY}K^b$/Ig complexes, half maximal stabilization can be seen at approximately 1 nM. In contrast, control peptide loaded MHC/Ig complexes, $^{VSV}K^b$/Ig or $^{MCMV}L^d$/Ig, do not specifically interact with T cells.

Thus, peptide loaded MHC/Ig molecules are very sensitive reagents in analyzing antigen-specific T cells.

EXAMPLE 4

This example demonstrates that divalent MHC/Ig contains the active fraction of MHC/Ig.

In light of the prior reported data indicating that tetravalent MHC was required for staining of class I restricted, antigen-specific T cells, we entertained the possibility that T cell staining with the $^{pep}$MHC/Ig complexes was due to staining by aggregated fractions of the $^{pep}$MHC/Ig complexes. To address this question, we fractionated the $^{pep}$MHC/Ig molecules by size exclusion chromatography (SEC) and analyzed each fraction for the ability to stain antigen-specific T cells.

Figure 6:
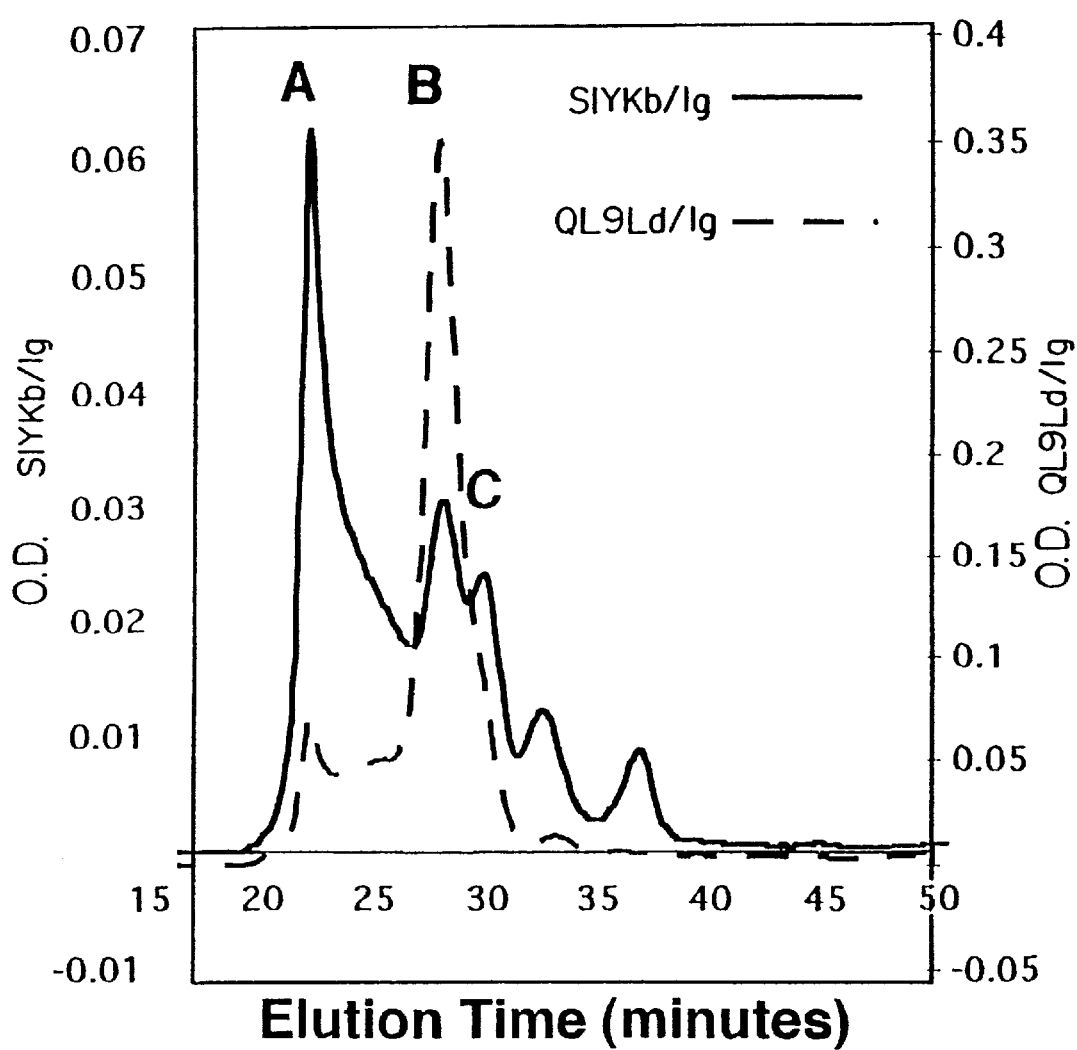
FIG. 6. SEC Analysis of peptide loaded MHC/Ig molecules. Approximately 50 $\mu$g of $^{siy}K^b$/Ig or $^{QL9}L^d$/Ig molecules were loaded onto a size exclusion chromatography column (Superdex 200, Pharmacia Biotech). The column was run with a PBS running buffer at 0.4 ml/min. on a BioLogic chromatography system (BioRad, Hercules, Calif.) with fractions collected every 0.4 ml. O.D. 280 are plotted for both the chimeric proteins.

Initial SEC experiments indicated a variety of protein peaks in preparations of $^{pep}$MHC/Ig molecules (FIG. 6). Both peptide loaded $L^d$/IgG and $K^b$/IgG had significant amounts of aggregated material (Peak A), with protein molecular weight >6.6×10$^5$. Interestingly, the different chimeric proteins had different amounts of protein found in the aggregates.

A second peak with a molecular weight of 2.6×10$^5$ $K^b$ was found and represented the monomeric divalent $^{pep}$MHC/Ig peak (peak B). In the divalent $L^d$/Ig protein this was the prominent protein peak. This peak represented a significant but smaller fraction of protein associated with $^{SIY}K^b$/Ig. In addition to aggregates and monomeric protein complexes, additional breakdown products were found in certain $^{pep}$MHC/Ig preparations. Peak C probably represents the breakdown of the chimeric molecule to IgG fraction and D and E represent smaller breakdown products that were also evident in the $^{SIY}$Kb/Ig preparation.

Figure 7:
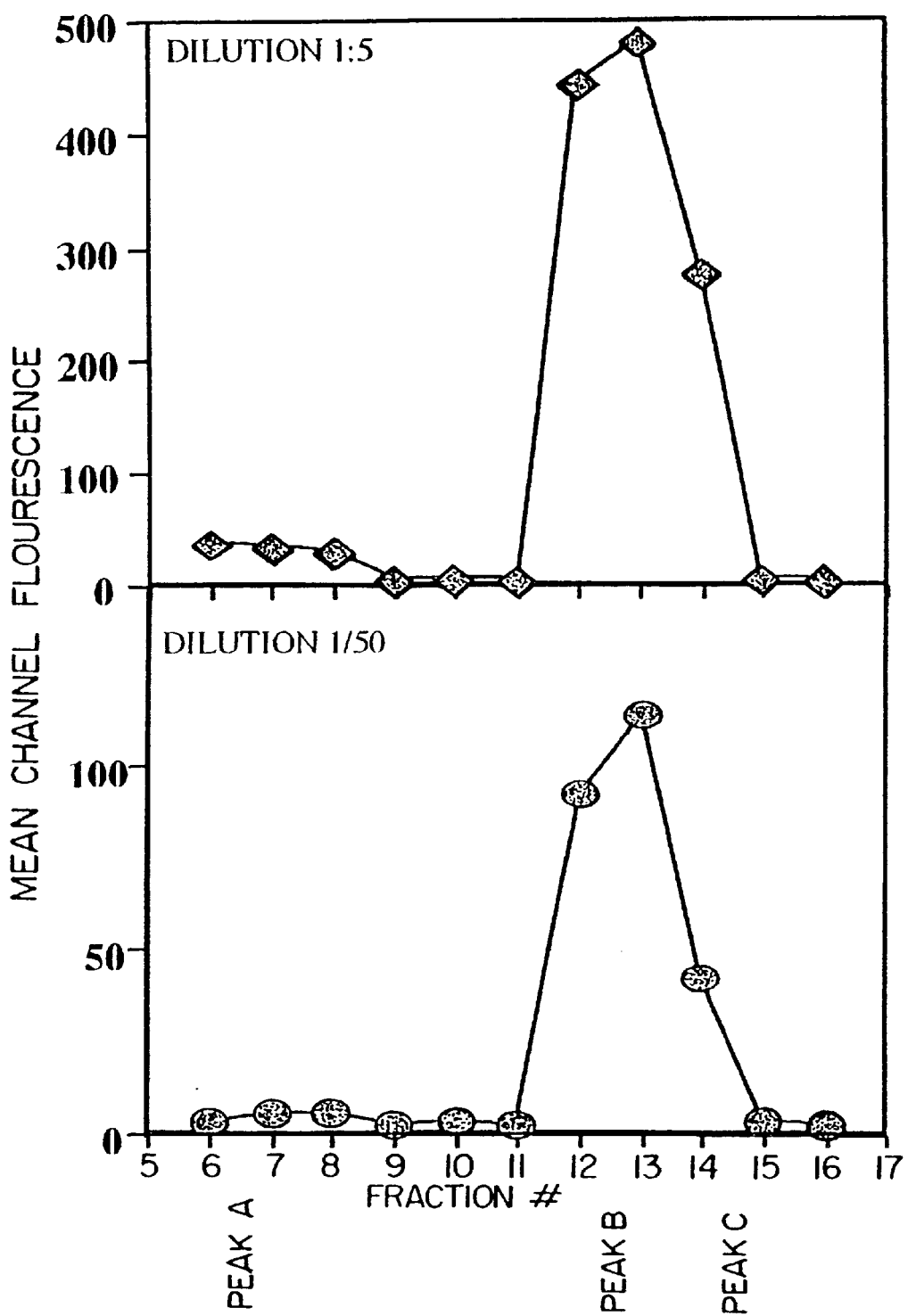
FIG. 7. Staining of 2C CTL is due to the monomeric fraction of $^{SIY}K^b$/Ig. $K^b$/Ig molecules were loaded with SIY peptide, 100 $\mu$M final concentration, as described. Viable T cells were purified using lymphocyte-M separation and reacted with either ⅕ or ⅟₅₀ dilution of each fraction collected by a preparative SEC analysis of $^{SIY}K^b$/Ig (500 $\mu$g), as described above. Cells were incubated with each fraction collected from the SEC analysis for 1 hour at 4° C. Cells were than washed and stained with goat anti-mouse PE and analyzed by flow cytometry. Data shown are the mean channel fluorescence obtained from representative samples. The experiments were repeated at least twice. Representative data are presented.
Figure 8:
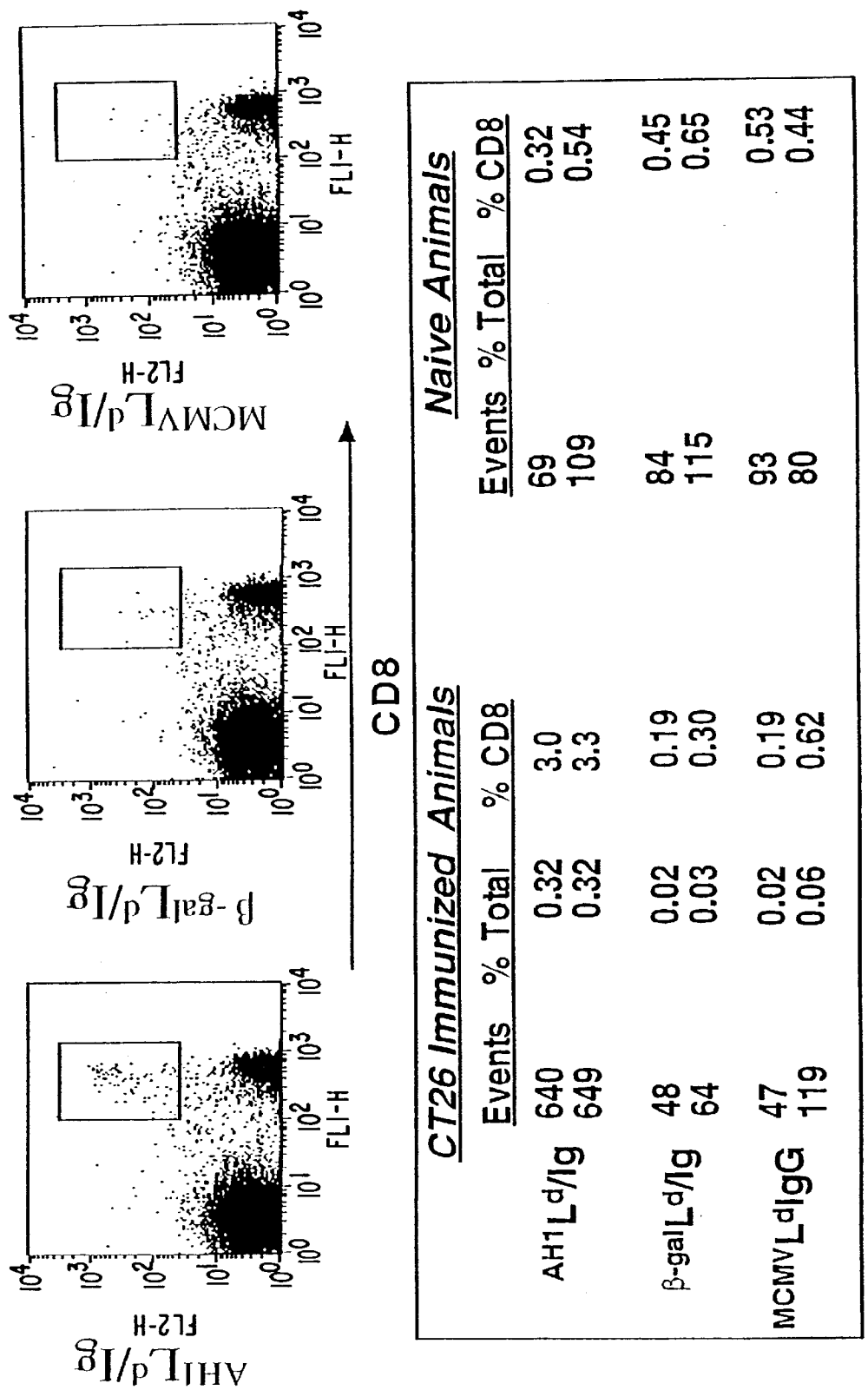
FIG. 8. Detection of AH1-specific T cells from spleen 14 days after vaccination with CT26-GM.

To determine which fraction was active in the flow cytometry assays, $^{pep}$MHC/Ig complexes were preparatively fractionated by SEC and tested for their ability to bind CTL. The dominant T cell binding activity was associated with the monomeric divalent MHC/Ig, protein peak B, and not the aggregated protein fraction (FIG. 7). While a limited amount of staining was observed with the aggregated material, protein peak A, this was relatively minimal and titered out rapidly. In contrast the monomeric peak containing the peptide loaded-divalent MHC/Ig fraction contained the overwhelming majority of the $^{pep}$MHC/Ig molecules responsible for CTL staining (FIG. 7).

Thus, using Ig as a molecular scaffold we have generated a high affinity divalent $^{pep}$MHC/Ig analog that can be used to stain antigen-specific T cells.

EXAMPLE 5

This example demonstrates detection of antigen-specific T cells from immunized animals.

Current approaches to monitoring antigen-specific T cells have distinct limitations associated with each approach. Monitoring of T cells requires use of broadly reactive monoclonal antibodies, such as anti-Vβ specific monoclonal antibodies, development of a highly specific anti-clonotypic monoclonal antibody, or use of an indirect cellular based assay. While highly specific, anti-clonotypic monoclonal antibodies are relatively rare and difficult to generate. In addition, while anti-clonotypic monoclonal antibodies will recognize an antigen-specific T cell expressing a specific TCR α/β complex, they do not recognize other antigen-specific T cells that see the same antigen/MHC complex using a different α/β TCR Cell-based assays, while specific for T cells recognizing an antigen/MHC complex of interest, are indirect assays and difficult to use to accurately define the number of T cells of interest. Thus, a major advance that $^{pep}$MHC/Ig complexes provide is the ability to directly identify antigen-specific T cells in development of an immune response.

We studied the ability to use $^{pep}$MHC/Ig complexes to analyze T cell repertoire in vivo by staining spleen cells from animals immunized with a model tumor vaccine, CT26-GM. CT26-GM is a murine colon carcinoma line that has been transfected with a gene encoding GM-CSF. When animals are immunized with CT26-GM they become resistant to growth of the parental CT26 tumor. This resistance is due to T cells that develop in immunized animals and that recognize a peptide antigen, AH1, presented in the context of H-2L$^d$ molecules. AH1 peptides are derived from an endogenous murine retrovirus whose sequence we have previously defined and which is known to bind effectively to H-2L$^d$ molecule and to sensitize T cells for development of an anti-CT26 immune response.

$^{pep}$MHC/Ig complexes efficiently detect antigen-specific T cells in animals immunized with CT26-GM. Fourteen days after a single immunization with CT26-GM cells, ~3% of all CD8$^+$ T cells are reactive with $^{AH1}$L$^d$/Ig complexes. Control $^{pep}$MHC/Ig complexes, $^{\beta\text{-}gal}$L$^d$/Ig and $^{MCMV}$L$^d$/Ig, are reactive with approximately 10-fold fewer cells, or 0.3% of all CD8$^+$ T cells. In a naive, nonimmunized animal, $^{AH1}$L$^d$/Ig complexes are only reactive with ~0.3% of all CD8$^+$ T cells. Therefore a single immunization leads to an approximately 10-fold increase in the total number of antigen-reactive T cells which could be detected using $^{pep}$MHC/Ig. Thus, $^{pep}$MHC/Ig can be used to monitor T cell homeostasis following immunization, transplantation, or during treatment of antigen-specific autoimmune diseases.

These results demonstrate that these reagents can be used with flow cytometry to specifically stain for T cells from lymphoid organs, peripheral blood, or other infiltrated tissues, as a means of directly and quantitatively assessing the number of antigen-specific T cells. Use of these reagents in combination with markers for activation provides a quantitative analysis of the activation state of these T cells. In addition, by using these reagents with a cell sorter, purified populations of antigen-specific T cells can be sorted. The purified populations can then be manipulated in vitro.

EXAMPLE 6

This example demonstrates that peptide loaded $^{Q19}$L$^d$/Ig or $^{SIY}$K$^b$/Ig specifically blocks lysis of target cells by 2C cytotoxic lymphocytes (CTL).

Figure 9:
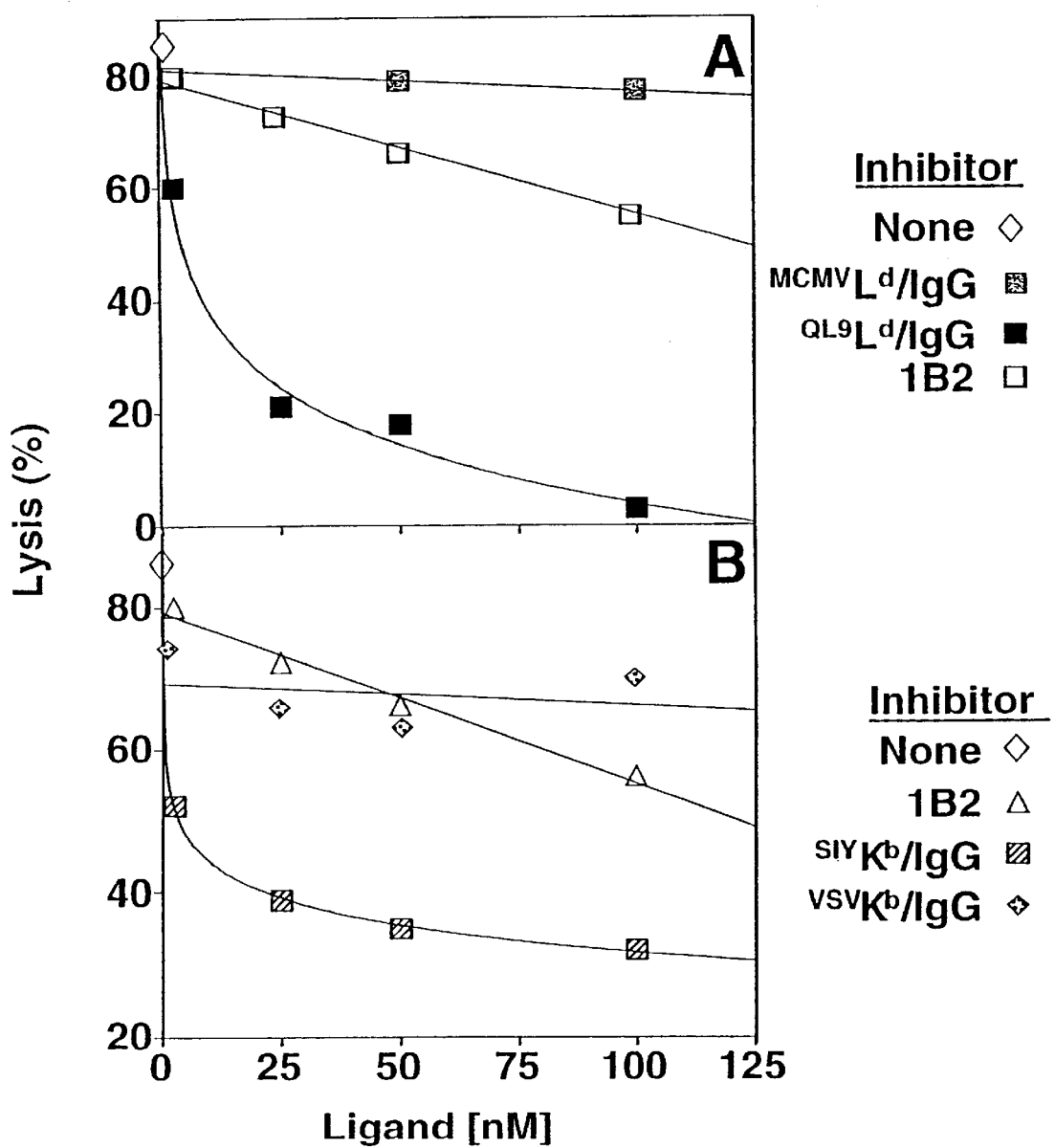
FIG. 9. $^{pep}$MHC/Ig complexes specifically inhibit peptide-dependent lysis of target cells by 2C CTL. Chromium labeled T2K$^{bm3}$ target cells were preincubated at 25° C. for 2.5 h with dEV8 peptide (10 nM). Concurrently, 2C T cells (3×10$^4$/well) were incubated with the indicated ligand at various concentrations for 1.5 h in V-bottom wells. After incubations, unwashed targets (3×10$^3$ per well) were added to the effectors/ligands, and the plates were subsequently incubated 4 h at 37° C. before harvesting and counting. Standard percent specific lysis was determined.

Using $^{Q19}$L$^d$/Ig as an inhibitor complex, target cell lysis was markedly inhibited, from 82% down to 2% (FIGS. 9A and 9B). Half maximal inhibition occurred at approximately 10 nM of $^{Q19}$L$^d$/Ig. Control $^{pep}$MHC/Ig complexes, $^{MCMV}$L$^d$/Ig, had no impact on lysis of target cells. The anticlonotypic monoclonal antibody, 1B2, was also used as a positive control antibody which inhibited CTL mediated lysis.

$^{SIY}$K$^b$/Ig also dramatically inhibited 2C CTL mediated lysis of target cells. In this case, maximal inhibition lowered specific lysis down from 85% to 35%. Inhibition of CTL mediated lysis is of particular importance, since CTL lytic activity can detect a very low concentration of antigen/MHC complexes on target cells. Thus, CTL-mediated lysis is considered very difficult to inhibit.

In addition to lysis of target cells, a variety of other physiologic responses, including T cell proliferation and lymphokine secretion, are associated with activation of CD8$^+$ T cell activation. Peptide-loaded divalent MHC, $^{SIY}$K$^b$/IgG, also inhibited T cell proliferation of 2C CTL stimulated by allogeneic splenic cells. Maximal inhibition was seen at about 20 nM $^{SIY}$K$^b$/IgG; the stimulation index of untreated cells decreased from 100% to 10% for cells treated with 20 nM $^{SIY}$K$^b$/IgG. Half maximal inhibition was seen at approximately 1 nM $^{SIY}$K$^b$/IgG.

The ability to selectively block antigen-specific immune responses provides a means by which this reagent can be used, for example, to turn off pathogenic responses in autoimmune disease or responses that lead to rejection after organ transplantation.

Modification of these reagents can also be made to allow the reagents to specifically kill antigen-specific T cells as a more definitive way to suppress these antigen immune responses. For example, the reagent can be conjugated with a toxin molecule, such as ricin or the α chain of Psuedomonas endotoxin. According to such an embodiment, the toxin-conjugated reagent is either injected in vivo or applied in vitro. When the reagent binds to T cells specific for the peptide/MHC complex, the reagent is internalized. The toxin molecule then selectively kills the pathogenic T cell of interest.

EXAMPLE 7

This example demonstrates activation of antigen-specific cells.

Because $^{pep}$MHC/Ig complexes crosslink cell surface T cell receptors, $^{pep}$MHC/Ig complexes can also be used to stimulate T cells. Immobilization of $^{pep}$MHC/Ig can stimulate antigen-specific T cells. Thus, these reagents can be used to selectively activate antigen-specific T cells either in vitro or in vivo.

The reagents can be used to activate T cells in vitro, followed by adoptive transfer into a patient. Alternatively, the reagents can be injected into a patient as a means of activating tumor antigen-specific T cells in vivo. Thus, the reagents of the invention represent a potent therapeutic antigen-specific vaccine for cancer.

These reagents can also be used as immunotherapeutics for infectious diseases, such as fungal disease, microbacterial diseases, viral diseases such as HIV, or intracellular parasites to activate T cell specific for antigens expressed for these pathogens.

The reagents of the invention thus represent a means of activating a variety of antigen-specific T cell responses.

EXAMPLE 8

This example demonstrates the covalent linkage of peptides for expression as part of a class I MHC/Ig chimera.

Another modification that provides for more stable production of these multivalent MHC/Ig reagents loaded with peptides of interest is the covalent linkage of the peptide via a linker to the MHC molecule. For MHC class I molecules, this is most easily accomplished by linking the peptide to the amino terminus of β2 microglobulin. For MHC class II molecules, the peptide can be tethered via a linker to the amino terminus of the β chain of MHC class II, as previously described. Using these tethered peptide MHC constructs, the peptide of interest is closely linked to the MHC molecule via the tether. This linkage favors the specific binding of that peptide over other potentially interfering peptides in the serum or medium.

Figure 19:
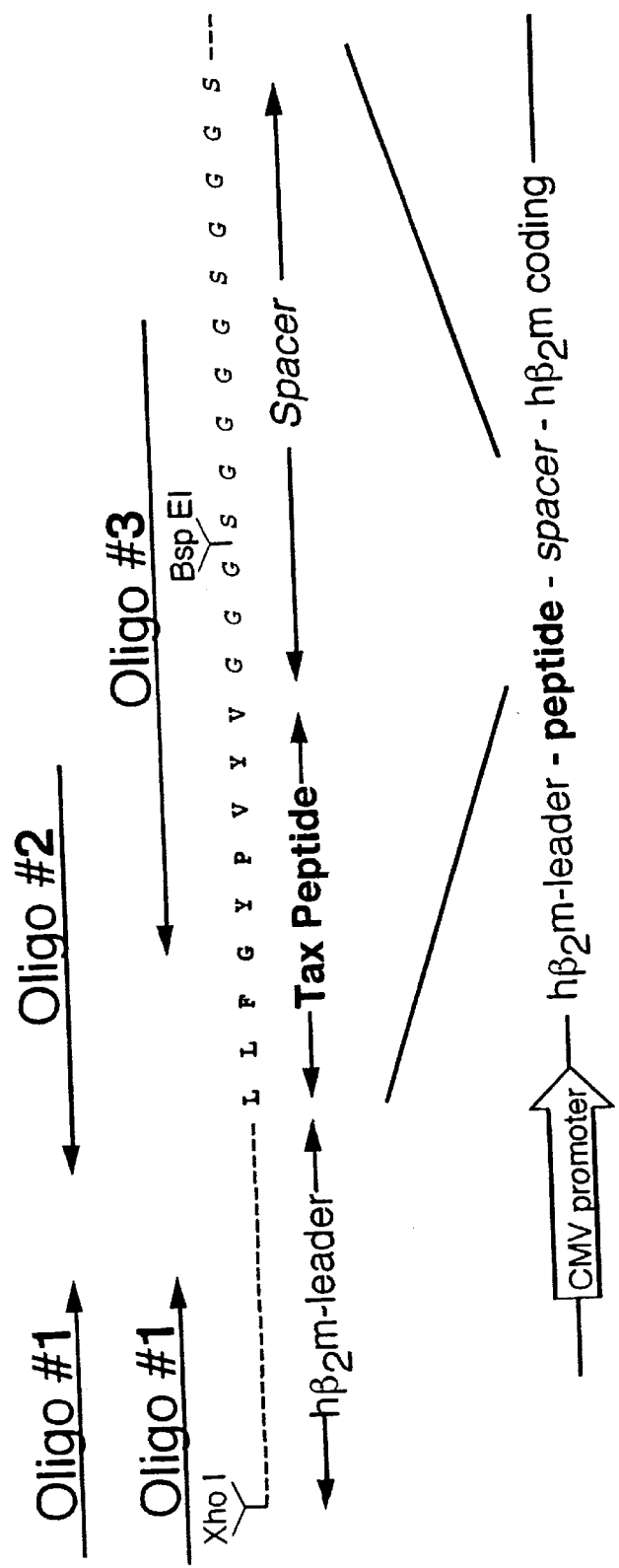
FIG. 19. Schematic oligo design used to generate peptides tethered to 2M.
Figure 20:
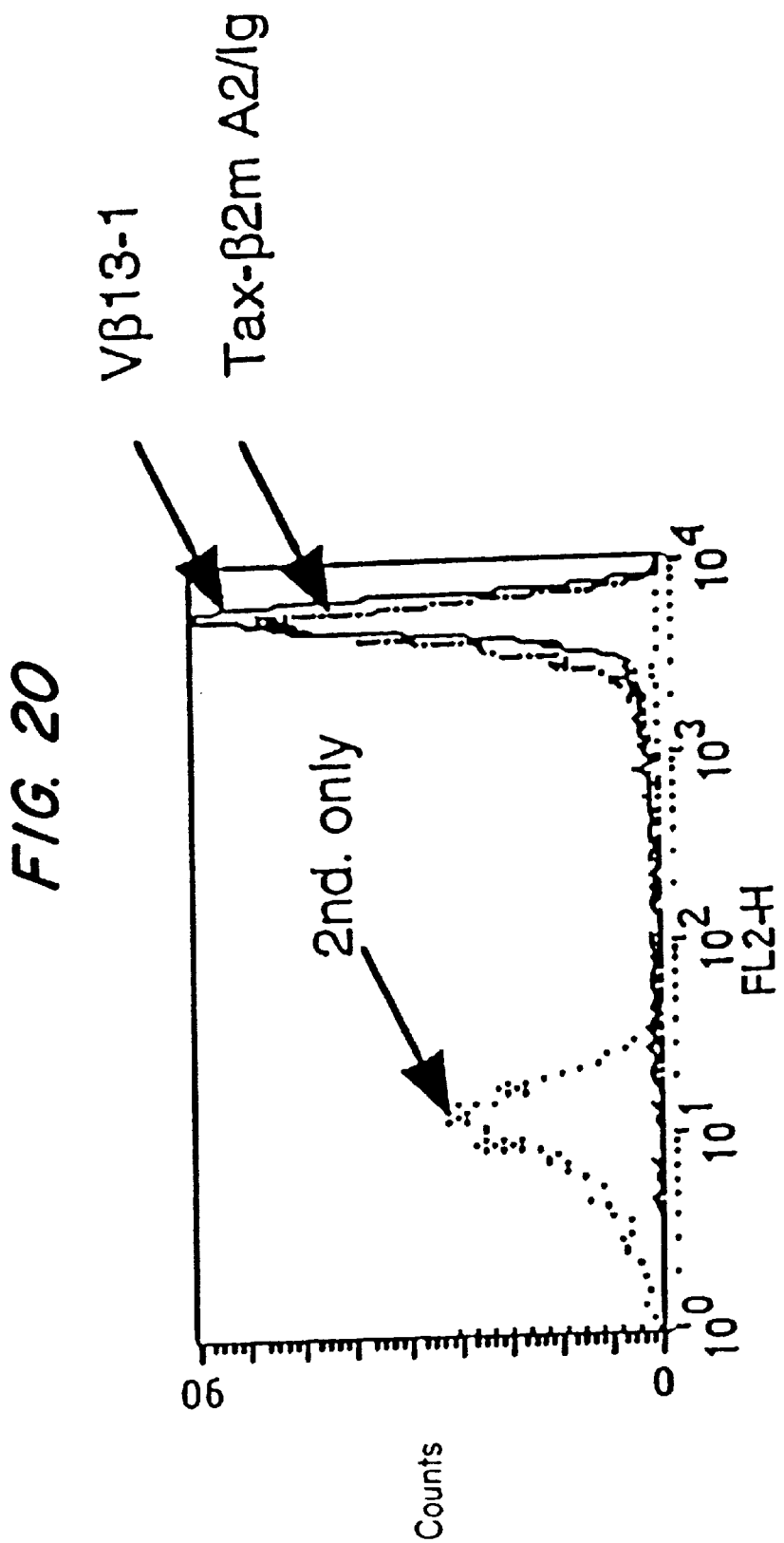
FIG. 20. Specific interaction of peptide-tethered tax-β2M HLA-A2/Ig complexes with HLA-A2 restricted CTL clones analyzed by flow cytometry. Mean channel fluorescence (MCF) of A6 cells stained with peptide tethered tax-β2M HLA-A2/Ig complexes was approximately 4000, MCF of A6 cells stained using no chimeric protein was only 10 and almost identical to staining controls with the control Gag-A2/Ig complex, unloaded HLA-A2/Ig. The level of staining with tax-β2M was similar to that obtained with an anti-Vβ13.1 specific mAb, indicating that all the relevant sites were saturated using tax-β2M HLA-A2/Ig. Thus, peptide tethering to β2M is an efficient way to present peptides in the context of MHC/Ig molecules.

To tether a peptide to the amino terminus of β2M, we have started by tethering a peptide derived from tax 11–19 to β2M (FIG. 19). The amino terminus of β2M was modified by genetically linking DNA encoding the linker with a convenient cloning site for insertion of different peptide into the amino terminus of β2M. A multiple round PCR-based mutagenesis was used to generate the peptide tethered to β2M. Oligonucleotides 1 and 2 were used to generate a small PCR fragment containing the human β2M leader fused to the tax 11–19 peptide. This PCR product was then used as a template for another PCR reaction using oligos 1 and 3. The PCR fragment generated from this second reaction covers the entire region, approximately 110 base pairs, between the Xho I and Bsp EI cloning sites.

This fragment was digested and cloned into the modified human β2M construct. Using this construct one can easily cassette in any peptide of interest to the amino terminus of β(2M. For expression, the modified human β2M cDNA was cloned into pcDNA3.1/Zeo- and cotransfected with the chimeric HLA-A2/Ig construct into J558L cells. Resultant cells can be selected with both G418 and Zeocin to ensure expression of both the chimeric HLA-A2/Ig and β2M polypeptides.

Peptide-tethered tax-β2M complexed with HLA-A2/Ig was specific in its interaction with HLA-A2 restricted CTL clones analyzed by flow cytometry. Thus, Tax tethered-A2/Ig was specifically reactive with an HLA-A2-restricted, HTLV-1 Tax 11–19-specific CTL clone, A6 (22). Mean channel fluorescence (MCF) of A6 cells stained with peptide tethered tax-β2M HLA-A2/Ig complexes was approximately 4000, MCF of A6 cells stained using no chimeric protein was only 10 and almost identical to staining controls with the control Gag-A2/Ig complex, unloaded HLA-A2/Ig. The level of staining with tax-b2M was similar to that obtained with an anti-Vβ13.1 specific mAb, indicating that all the relevant sites were saturated using tax-β2M HLA-A2/Ig. Thus peptide tethering to β2M is an efficient way to present peptides in the context of MHC/Ig molecules.

Direct Visualization of Antigen-specific T Cells in HTLV-1-Associated Myelopathy/Tropical Spastic Paraparesis The following examples demonstrate the use of reagents of the invention to visualize directly antigen-specific T cells in patients with HTLV-1-associated myelopathy/tropical spastic paraparesis (HAM/TSP) and HIV infections.

HAM/TSP is caused by a human retrovirus, human T lymphotropic virus type I (HTLV-1) (2, 3). The clinical symptoms of HAM/TSP are characterized by upper motor neuron signs and mild sensory and sphincter dysfunction (3). Histopathologically, one finds thoracic spinal cord atrophy involving perivascular demyelination and axonal degeneration (4, 5). The pathophysiology of HAM/TSP is still not completely understood (6). Serum reactivity to HTLV-1 was first associated with HAM/TSP by Osame and coworkers in 1986 (3). The immunologic hallmark of patients with HAM/TSP is the spontaneous proliferation of peripheral-blood lymphocytes (PBL) in vitro (7–9).

It has been previously demonstrated that circulating $CD8^+$ cytotoxic T lymphocytes (CTL) in patients with HAM/TSP react against HTLV-1 protein products (10) and an immunodominant HLA-A2-restricted epitope (HTLV-1 Tax11–19) has been well characterized (11). HTLV-1 Tax11–19-specific CTL precursor frequency was estimated by limiting dilution analysis in the range of 1/75 to 1/320 $CD8^+$ lymphocytes (12) in peripheral blood. Tax-specific CTL were also found in cerebrospinal fluid (CSF) (12, 13) and HTLV-1 specific clones could be generated in vitro from a spinal cord lesion that was obtained from a HAM/TSP patient (14).

Immunohistochemical analysis of affected spinal cord lesions in the early stage of the disease from patients with HAM/TSP reveals the presence of infiltrating $CD4^+$ and $CD8^+$ lymphocytes, in which the $CD8^+$ population predominates with duration of the disease (15). Moreover an increase in activated lymphocytes has been shown in PBL and CSF (16, 17). Recently, we have been able to demonstrate that peripheral $CD8^+$ T lymphocytes produce IL-2, IFN-γ and TNF-α in HAM/TSP patients (18). Collectively, this evidence has supported the view that virus-specific $CD8^+$ T lymphocytes may play a critical role in the immunopathogenesis of HAM/TSP.

One major limitation in these studies has been the inability to identify HTLV-1 specific $CD8^+$ T cells directly from biological samples not only to quantitate the actual number of antigen-specific T cells in vivo but also to further characterize the antigen-specific population of T lymphocytes without in vitro amplification. To overcome these problems, we have developed divalent MHC class I constructs using immunoglobulin as a scaffold (20) and used these to elucidate the role of antigen-specific $CD8^+$ T cells in different human immunologic diseases, such as HAM/TSP.

The examples below demonstrate our analysis of HTLV-1 Tax11–19- and p17 Gag77–85-specific, $HLA-A2^+$-restricted $CD8^+$ T lymphocytes directly from peripheral blood and cerebrospinal fluid using peptide-loaded divalent HLA-A2/Ig chimeras.

EXAMPLE 9

This example demonstrates materials and methods used to analyze $HLA-A2^+$-restricted $CD8^+$ T lymphocytes specific for HTLV-1 Tax11–19 or p17 Gag77–85 directly from peripheral blood and cerebrospinal fluid using peptide-loaded divalent HLA-A2/Ig chimeras.

Study subjects and specimens. Clinical characteristics of patients with HAM/TSP and asymptomatic HTLV-1 infected individuals as well as HLA type were previously described (12) and are summarized in Table 1. HTLV-1 infection was confirmed by Western Blot in serum of HAM/TSP patients and asymptomatic carriers. Diagnosis of HAM/TSP was made according to WHO criteria, by reference to neurological symptoms and serological testing of HTLV-1.

PBL were prepared by Ficoll-Hypaque centrifugation and stored in liquid nitrogen until use. Histocompatibility typing was performed on PBL or EBV-transformed lymphoblastoid cell lines by the Tissue Typing Laboratory at the NIH Clinical Center. Some of the healthy HLA-A2 uninfected controls were tested for HLA-A2 expression by FACS analysis using a panel of HLA-A2-specific monoclonal antibodies: MA2.1, BB7.2 and PA2.1 (American Type Culture Collection, Rockville, Md.).

Peptides. Peptides HTLV-1 Tax11–19 (LLFGYPVYV) (SEQ ID NO:1), influenza virus A M158–66 (GILGFVFTL) (SEQ ID NO:2), and p17 Gag77–85 (SLYNTVATL) (SEQ ID NO:3) were synthesized and HPLC purified at the Colorado State University Macromolecular Resources. Identity of the peptides was confirmed by mass spectrometry measurement.

Cloning the construct and protein expression. Using oligonucleotide-directed PCR, we introduced a 5' Mlu I and a 3' Not I site (sites underlined) into the extracellular domain (α1–α3) of HLA-A2 cDNA using the following primer pair: 5'-GAT<u>ACGCGT</u>TGGGCTCTCACTCCATGAG (SEQ ID NO:4) and 5'-CAGTCGAT<u>GCGGCCGC</u>CCATCTCAG GGTGAGGGGCT (SEQ ID NO:5). After PCR amplification, the α1–α3 region of HLA-A2 was sequenced and directionally cloned in exchange for $H-2K^b$ into the previously described pX/Ig vector (20).

The construct was cotransfected with DNA encoding the chimeric HLA-A2/Ig protein and the human β2-microglobulin by electroporation into J558L cells. Transfectants were screened for secretion of the chimeric protein by ELISA as previously described (20). ELISA plates were coated with BB7.2, an antibody specific for peptide-loaded conformations of HLA-A2, or with a goat anti-mouse IgG-Fc antibody (10 µg/ml) (Cappel, Durham, N.C.). High secretors were picked and grown in Hybridoma-SFM (Gibco-BRL, Gaithersburg, Md.). HLA-A2/Ig secretion from the transfected J558L was confirmed by SDS-PAGE electrophoresis.

The chimeric protein was harvested from cell supernatant and was concentrated with Centriflo®-membrane cones (Amicon, Beverly, Mass.). HLA-A2/Ig was loaded with 660 fold-molar excess of peptide for 10–14 days prior to FACS analysis. Three µg of protein was used for staining of $1\times10^6$ cells.

Flow Cytometric Analysis. Murine monoclonal anti-human CD8-FITC (Sigma, St. Louis, Mo.), anti CD-4 PE (Becton Dickinson, San Jose, Calif.), anti-CD8-Tri (Caltag Laboratories, Burlingame, Calif.), and anti-HLA-DR (Pharmingen, San Diego, Calif.) were used to detect cell surface molecules of lymphocytes. PK1.36-FITC was used as an isotype-matched control for anti-HLA DR-FITC. HLA-A2/Ig bound onto the cell surface was detected using goat-anti-mouse IgG1-PE or a goat-anti-mouse IgG1-Tri (Caltag). Monoclonal anti-TNF-α-FITC, anti-IFN-γ-FITC, or isotype-matched IgG1-FITC antibodies (Pharmingen) were used for intracellular cytokine staining. PBL ($1\times10^6$) were incubated with peptide-loaded HLA-A2/Ig on ice, followed by PE or Tri-conjugated goat-anti mouse IgG1-PE.

Intracellular staining was performed according to the manufacturer's instructions with slight modifications (21) after a 4 hour incubation at 37° C., followed by a 10 h incubation in the presence of 10 µg/ml brefeldin A (Sigma). Three-color fluorimetric analysis was carried out on a FAC-Scan (Becton Dickinson). Lymphocytes were gated on forward and side scatter. $1\times10^5$ ($2\times10^5$ for three-color analysis) gated events were analyzed using CELLQuest software (Becton Dickinson). PBL from all HLA-A2 positive patients were stained at least twice with similar results.

EXAMPLE 10

This example demonstrates that peptide-loaded HLA A2/Ig binds specifically HLA-A2 restricted CTL.

Figure 11A:
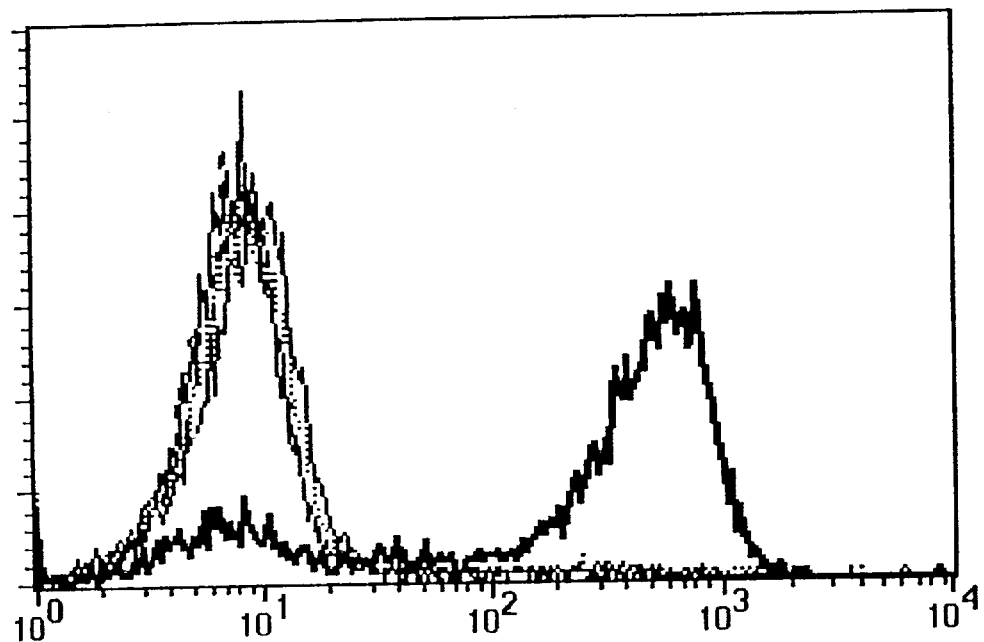
FIG. 11A. FACS analysis was carried out using A6 cells (22), specific for the immunodominant HLA-A2 restricted Tax epitope Tax11–19. HTLV-1 Tax11–19 loaded HLA-A2/IgG stably bound on the cell surface and was detected using PE-labeled goat-anti mouse Ig (heavy line). Gag-A2/Ig was used as an irrelevant control (thin line) as well as no HLA-A2/Ig, unloaded HLA-A2/Ig and M1-loaded HLA-A2/Ig (dotted and stripped lines overlapping).
Figure 11B:
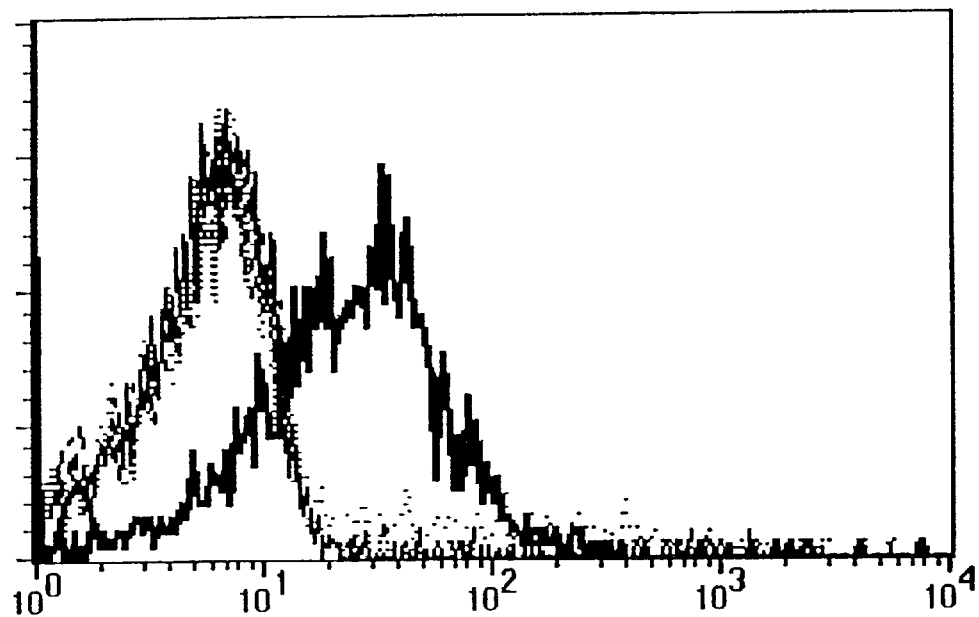
FIG. 11B. T cells specific for the HLA-A2-restricted HIV p17 Gag 77–85 epitope were stained to demonstrate the peptide-specificity of peptide-loaded HLA-A2/Ig. Gag77–85 loaded HLA-A2/IgG was stably bound on the cell surface and detected using PE-labeled goat-anti mouse Ig (heavy line). HTLV-1 Tax11–19 loaded HLA-A2/Ig as well as no peptide loaded, M1-loaded HLA-A2/Ig, and no HLA-A2/Ig were used as an irrelevant control and stained virtually identical (overlapping thin, dotted and stripped lines).

We have engineered a divalent HLA-A2/Ig molecule, using immunoglobulin as a scaffold, that can be loaded with various peptides. Peptide-loaded HLA-A2/Ig was specific in its interaction with HLA-A2 restricted CTL clones analyzed by flow cytometry. Thus, Tax-A2/Ig was specifically reactive with an HLA-A2-restricted, HTLV-1 Tax11–19-specific CTL clone, A6 (22). Mean channel fluorescence (MCF) of A6 cells stained with HTLV-1 Tax11–19 loaded HLA-A2/Ig (Tax-A2/Ig) was 426, while MCF of A6 cells stained with the control Gag-A2/Ig complex was only 13 and almost identical to staining controls using no chimeric protein, unloaded HLA-A2/Ig, or M1-loaded HLA-A2/Ig (FIG. 11A). In complementary experiments, Gag-A2/Ig specifically stained the HIV p17 Gag 77–85-specific clone SL09 (23) (FIG. 11B), while staining with Tax-A2/Ig was virtually identical to unloaded HLA-A2/Ig, M1-loaded HLA-A2/Ig, or no HLA-A2/Ig.

EXAMPLE 11

This example demonstrates visualization of antigen-specific T lymphocytes in peripheral blood of patients with HAM/TSP and HIV infections.

HTLV-1 Tax11–19-specific CTL activity has been demonstrated directly in PBL from HAM/TSP patients (10). In HLA-A2$^+$ patients, HTLV-1-specific reactivity is predominately directed against the HTLV-1 Tax11–19 epitope (11). Previous estimates of precursor frequencies of HTLV-1 Tax11–19-specific CTL using limiting dilution analysis (LDA) gave values in the range of 1/75 to 1/320 CD8$^+$ T cells.

Figure 12:
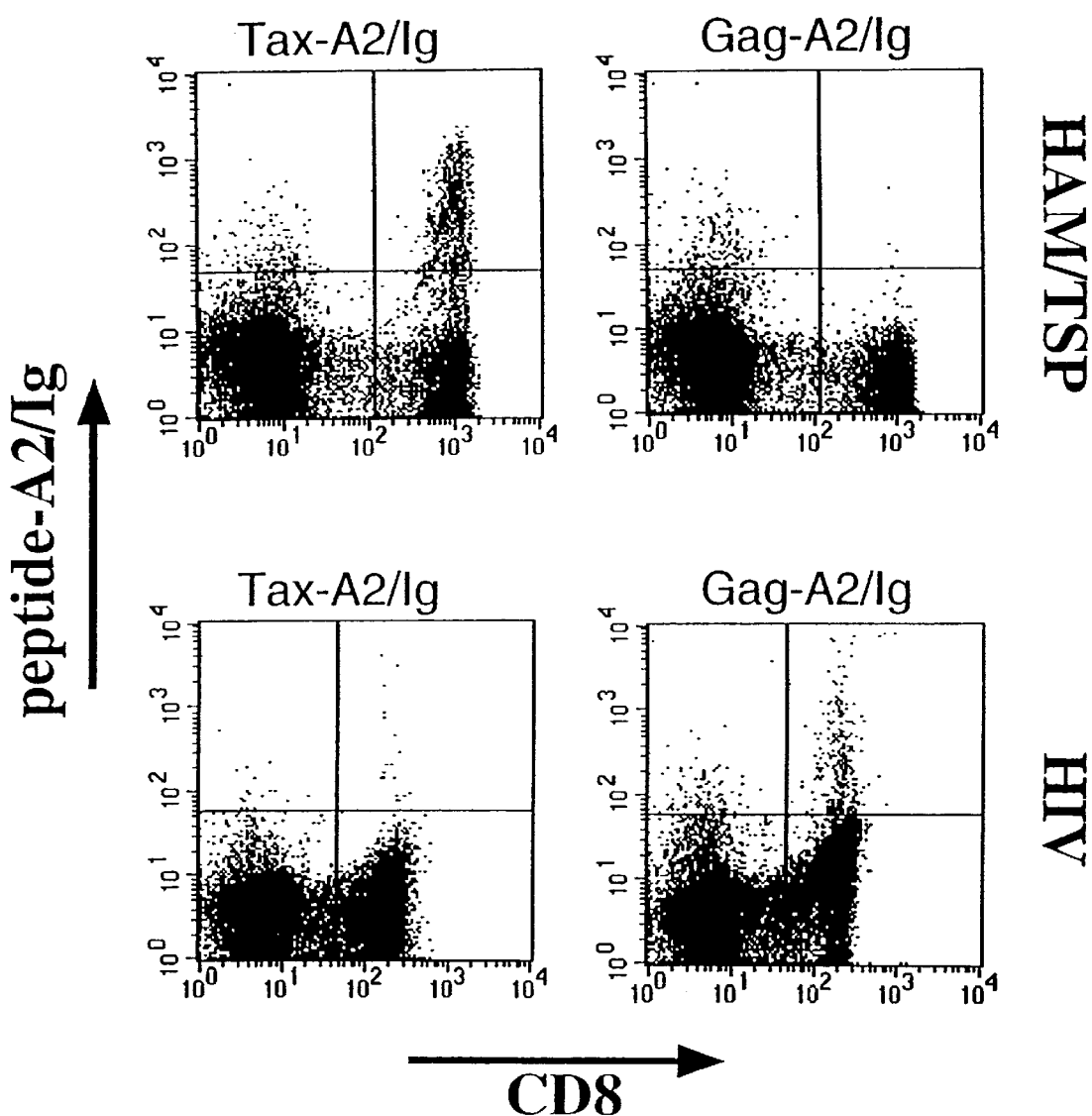
FIG. 12. Peptide loaded HLA-A2/Ig can be used to visualize antigen-specific CD8$^+$ T cells in peripheral blood. Two-color flow cytometry was performed using Tax-A2/Ig or Gag-A2/Ig and mouse anti-human CD8-FITC. PE-labeled goat anti-mouse IgG1 monoclonal antibody was used to detect the peptide-A2/Ig complex. Frozen PBL from an HAM/TSP patient (donor H1 see Table 1) were examined. Anti-human CD8-FITC and Tax-A2/Ig positively stained 4.03% of the PBL from the HAM/TSP patient. This represents 10.49% of all CD8$^+$ cells. No significant signal was seen using Gag-A2/Ig (<0.1%). PBL from an HLA-A2$^+$ HIV-1 infected individual showed 3% Gag-A2/Ig positive CD8$^+$ T lymphocytes.
Figure 13:
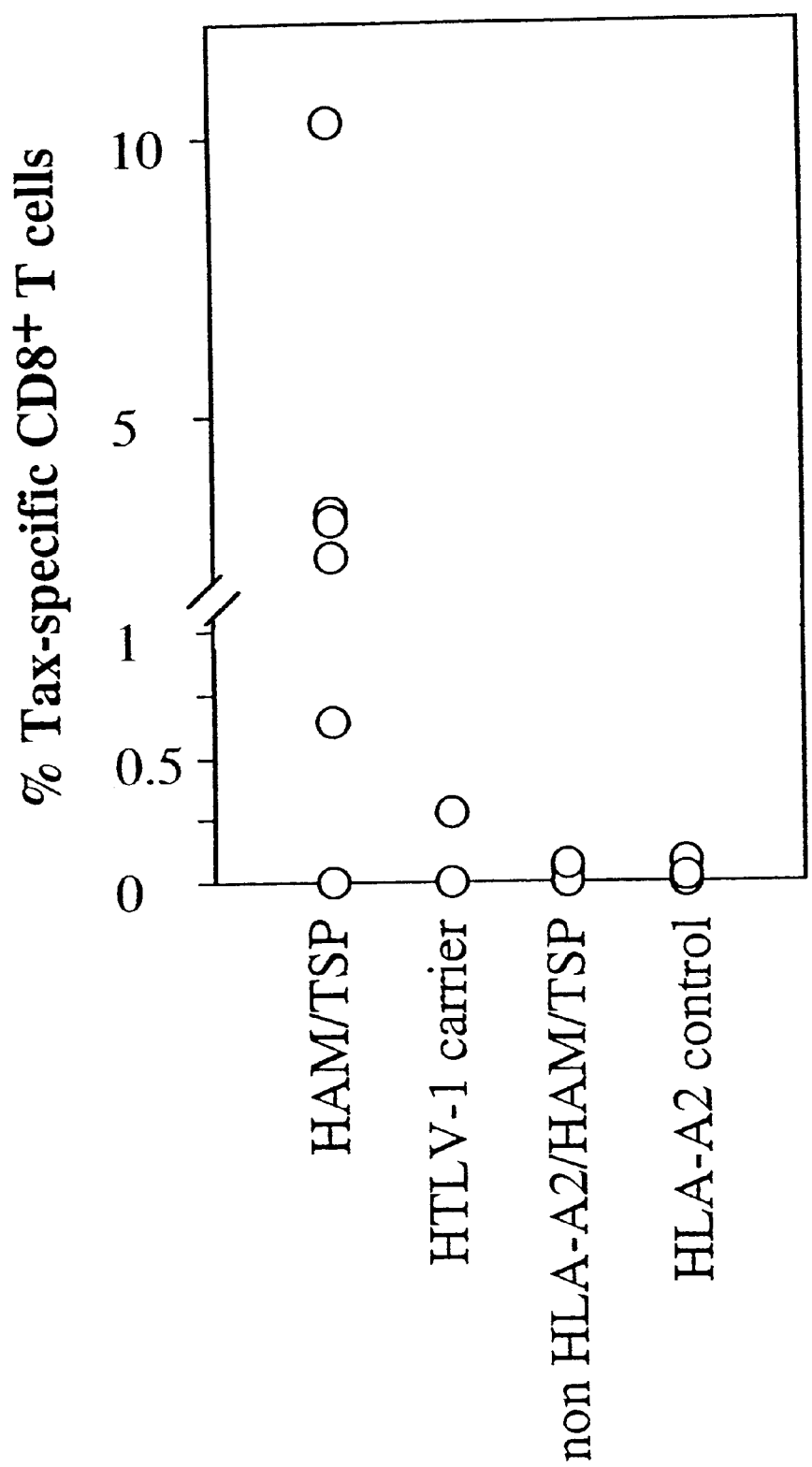
FIG. 13. HAM/TSP patients carry high numbers of HTLV-1 Tax11–19-specific CD8$^+$ cells in their PBL. The percent of HTLV-1 Tax11–19-specific, CD8$^+$ T cells from HLA-A2$^+$ HAM/TSP patients, HTLV-1 infected HLA-A2$^+$ carriers, HLA-A2$^-$ HAM/TSP patients, and healthy individuals are presented. Between 0.64 and 10.25% of the CD8$^+$ cells from HAM/TSP patients are specific for the HTLV-1 Tax11–19 peptide. One of the analyzed HTLV-1 infected donors had 0.33% Tax-specific CD8$^+$ cells, whereas no significant number of Tax-specific CD8$^+$ cells were found in non-HLA-A2 HAM/TSP donors or HLA-A2$^+$ healthy individuals. Positive samples were at least stained twice.

To quantitate directly the HTLV-1 Tax11–19-specific CD8$^+$ population in peripheral blood of HAM/TSP patients, we performed two dimensional flow cytometric analysis of cells using Tax-A2/Ig and anti-CD8$^+$ (FIG. 12). PBL from patients with HAM/TSP showed a significant high number of HTLV-1 Tax11–19 specific CD8$^+$ T lymphocytes. In one patient the frequency of Tax11–19-specific cells was as high as 13.8% (FIGS. 12 and 13 and Table 1). The percentage of Tax-A2/Ig specific cells ranged between 0.64 and 13.87% of CD8$^+$ T cells, with values >2% for 4 of the 6 HAM/TSP patients FIG. 12). CD8$^+$ T cells specific for p17 Gag77–85 could also be detected (FIG. 12, right panels).

In one of the six HLA-A2 positive HAM/TSP patients, no Tax-A2/Ig-reactive cells were detected. However, this same patient's PBL also did not lyse Tax protein-expressing, autologous, EBV transformed B cells (unpublished data). Moreover, we were able to detect Tax-specific T cells with Tax-A2/Ig in every patient sample that lysed Tax-expressing, HLA-A2$^+$ target cells (Table 1).

EXAMPLE 12

This example demonstrates analysis of peripheral blood from two HLA-A2$^+$ HTLV-1 carriers.

We also analyzed peripheral blood from two HLA-A2$^+$ HTLV-1 carriers who did not have HAM/TSP (FIG. 13 and Table 1). One of the two HTLV-1 carriers had no detectable HTLV-1 Tax11–19-specific T cells, while the other contained a low but reproducibly detectable number of CD8$^+$ T cells that stained with Tax-A2/Ig (0.33%).

To confirm the specificity of staining of peripheral blood samples with these reagents and their relationship to the disease, we analyzed PBL from HAM/TSP patients who do not carry the HLA-A2 allele (Table 1 and FIG. 13), uninfected healthy HLA-A2$^+$ donors (Table 1 and FIG. 13), and an HIV-1 infected HLA-A2$^+$ individual (FIG. 12). Less then 0.1% of CD8$^+$ T cells from all of these samples stained positively with the Tax-A2/Ig. However, a significant number (3.03%) of the CD8$^+$ T lymphocytes from the HIV-infected individual was stained using Gag-A2/Ig.

Collectively, these results demonstrate that the presence of high numbers of Tax-A2/Ig staining CD8$^+$ cells is specific for HTLV-1$^+$ HLA-A2$^+$ individuals with HAM/TSP.

EXAMPLE 13

This example demonstrates visualization of antigen-specific T lymphocytes in cerebrospinal fluid of patients with HAM/TSP.

Figure 14A:
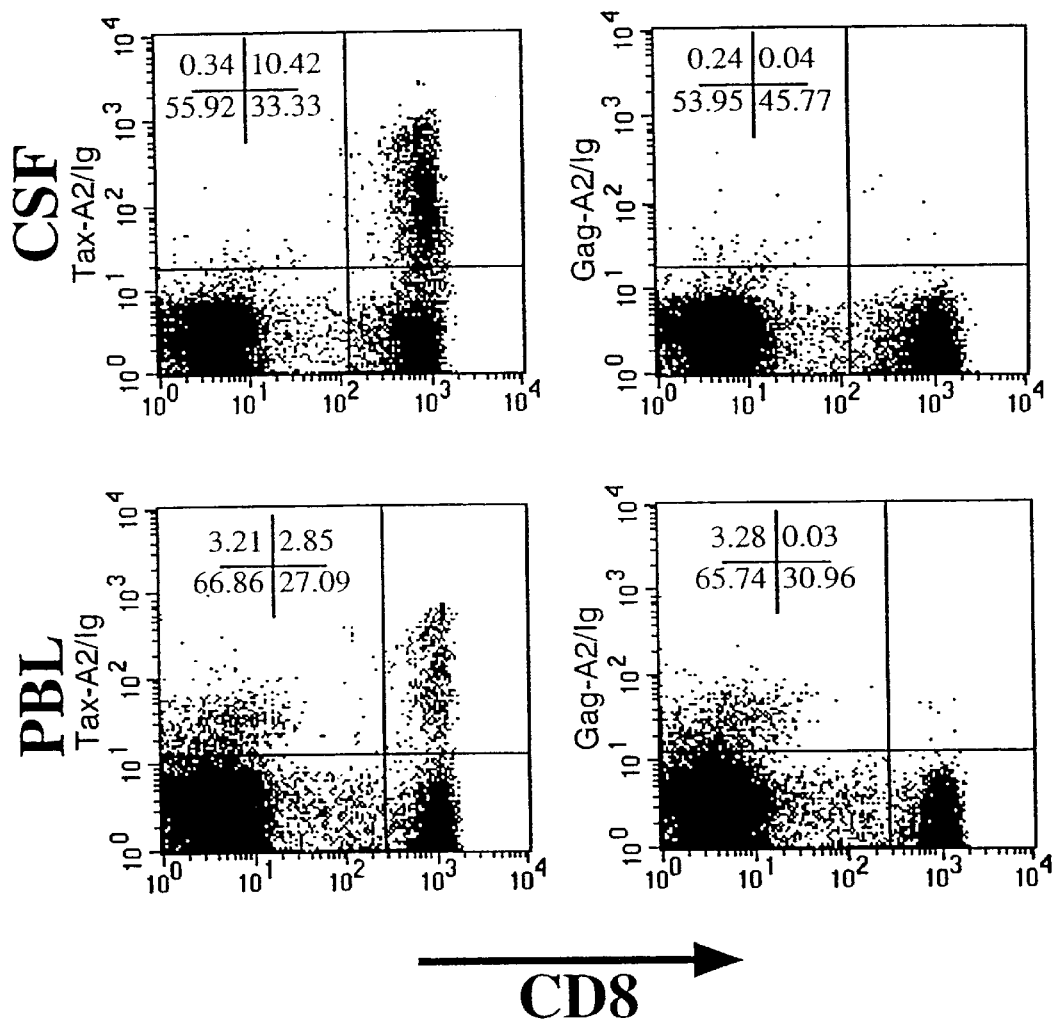
FIG. 14A. Of the CD8$^+$ T cells in cerebrospinal fluid, 23.7% were Tax-specific, and only 9.4% of the CD8$^+$ T cells from peripheral blood were Tax-specific. No significant signal was seen using Gag-A2/Ig (<0.1%).

To corroborate the significance of HTLV-I-specific CTLs for the pathogenesis of this demyelinating disease, we analyzed lymphocytes from cerebrospinal fluid of a patients with HAM/TSP (H1) and compared them with the T cells in his peripheral blood from the same day. Tax-A2/Ig-specific CD8$^+$ cells constituted 23.7% of the CD8$^+$ cell population in cerebrospinal fluid were. In contrast, we detected 9.4% Tax-A2/Ig specific CD8+T cells in the peripheral blood (FIG. 14A). Interestingly, we found the same number of CD4$^+$ T cells in peripheral blood and cerebrospinal fluid (44% in the PBL and 48% in the CSF), but also an increased number in total CD8$^+$ T cells in the CSF (42%) compared to the peripheral blood (29%) (FIG. 14B).

EXAMPLE 14

This example demonstrates that HTLV-1 Tax11–19-specific T cells in patients with HAM/TSP are activated.

The ability to stain HTLV-1 Tax11–19-specific T lymphocytes directly provides the opportunity to analyze their state of activation. If HTLV-1-specific CD8+ T cells indeed mediate the immunopathogenesis of HAM/TSP, a significant proportion of them might be expected to be activated. Since activated human T cells express elevated levels of MHC class II molecules, we further characterized the HTLV-1 Tax11–19-specific T cells from HAM/TSP patients for HLA-DR expression by multicolor flow cytometry.

Tax-A2/Ig reactive, CD8+ T cells from the 3 HAM/TSP patients had significantly increased expression of DR (FIG. 15). In 2 of 3 patients, the level of DR expression was virtually identical to that seen in control PHA-stimulated PBL (compare FIGS. 15A and 15B, Tax-A2/Ig reactive-specific CD8+ T cells from patients, to FIG. 15E, activated human PBL). Similar results were obtained for IL-2 receptor expression (data not shown).

Of particular interest, one patient, H6, demonstrated a significantly lower population of DR+, Tax-specific CD8+ cells FIG. 15C). This individual, the spouse of a HAM/TSP patient, was originally thought to be an asymptomatic carrier, since no neurologic symptoms were reported. However, on a physical examination a hyperreflexia in the lower extremities and extensor plantar responses were observed, indicative of corticospinal tract lesion(s).

EXAMPLE 15

This example demonstrates expression of cytokines by Tax-specific CD8+ cells from HAM/TSP patients.

Inflammatory cytokines are considered critical mediators of CNS immunopathology in many autoimmune models. Elevated levels of several proinflammatory cytokines have been detected in the serum or cerebrospinal fluid of HAM/TSP patients (16, 17). Therefore it is of particular interest to analyze Tax-specific CD8+ cells from HAM/TSP patients for the presence of relevant intracellular cytokines.

Recently, we have found that bulk CD8+ T cells from HAM/TSP patients demonstrated significant expression of cytokines, such as TNF-α, IFN-γ, and IL-2 but not IL-4 (18). Tax-specific CD8+ T cells from patients H1 (FIG. 16), H5 (data not shown), and H6 (FIG. 16) demonstrated distinct patterns of intracellular TNF-α and IFN-γ expression. While the HAM/TSP patients H1 and H5 displayed a high proportion of Tax-A2/Ig-specific, CD8+ cells with intracellular TNF-a and IFN-g (roughly 30%), patient H6 had a very low proportion of Tax-specific CD8+ cells expressing intercellular TNF-a and IFN-g (2%).

These results, together with HLA-DR analysis, demonstrate a disassociation between expansion of antigen-specific T cells and their activation state. They further demonstrate how the ability to use multiparameter flow cytometry to analyze the activation state of antigen-specific T cell populations can provide further insight into the relationship between state of T cell activation and disease pathogenesis.

EXAMPLE 16

This example demonstrates that Tax-Specific CD8+ T Cells Persist in Peripheral Blood from HAM/TSP Patients.

An important aspect in understanding the pathogenesis of autoimmune diseases, such as HAM/TSP is to understand the dynamics of antigen-specific T cell responses. We therefore compared the numbers of Tax-specific, CD8+ T cells from a HAM/TSP patient (H1) who had serial PBL drawn between 1989 and 1998. This patient was initially diagnosed in 1979.

Figure 17:
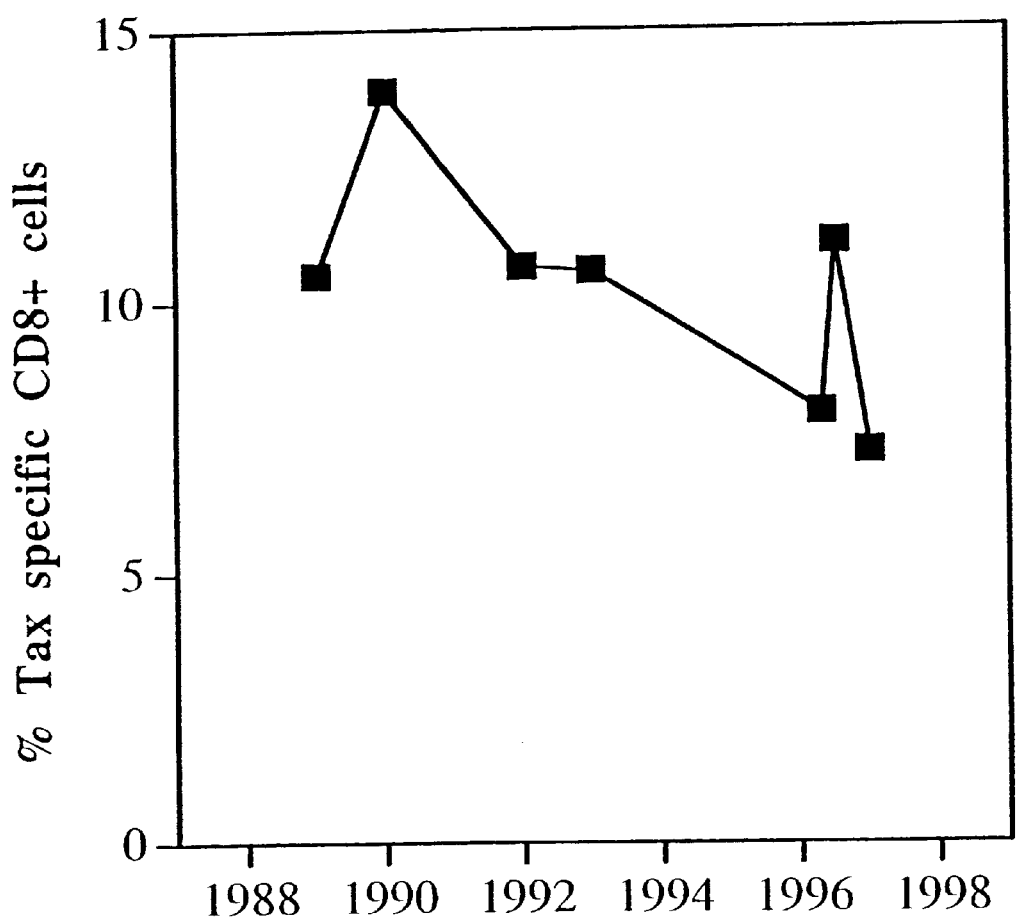
FIG. 17. High levels of HTLV-1 Tax-specific CD8+ T lymphocytes persist during HAM/TSP. PBL samples obtained between 1989 and 1998 from patient H1 were analyzed for Tax-specific, CD8$^+$ cells. Between 7.24 and 13.87% specific CD8+ T cells were detected in the frozen PBL samples.

Interestingly, even 10 years after diagnosis, this patient had about 10% Tax-specific CD8+ T cells. This percentage did not change significantly over the next eight years (FIG. 17).

Thus, in this patient, pathogenic Tax-specific CD8+ T cells are sustained at high levels even after 19 years of active disease.

TABLE 1

| Donor | Gender/Age | clinical status[1] | duration of disease (years) | HLA-A | CTL activity[2] | CD8+ | Tax+ CD8+[3] | M1+ CD8+[4] | % Tax-spec. CD8+[5] |
|---|---|---|---|---|---|---|---|---|---|
| H1[6] | M/52-60 | HAM/TSP | 15–23 | A2, 28 | + | 21.46 | 2.52 | 0.04 | 7.24–13.87 |
| H2 | F/47 | HAM/TSP | 16 | A2, 33 | + | 21.14 | 0.18 | 0.04 | 0.64 |
| H3 | F/48 | HAM/TSP | 2 | A2, 3 | − | 16.66 | 0.02 | 0.02 | 0 |
| H4 | M/58 | HAM/TSP | 14 | A2, 66 | + | 24.52 | 0.82 | 0.04 | 3.08 |
| H5 | F/51 | HAM/TSP | 16 | A2, 3 | + | 14.85 | 0.49 | 0.04 | 2.94 |
| H6 | F/77 | HAM/TSP | 4 | A1, 2 | + | 45.38 | 1.62 | 0.10 | 3.23 |
| C1 | F/54 | carrier | — | A2, 11 | + | 21.41 | 0.10 | 0.03 | 0.33 |
| C2 | F/52 | carrier | — | A2, 24 | − | 22.33 | 0.01 | 0.01 | 0 |
| 1 | n.d. | healthy | — | A2 | − | 41.48 | 0.03 | 0.02 | 0.02 |
| 2 | n.d. | healthy | — | A2 | n.d. | 22.31 | 0.03 | 0.13 | 0 |
| 3 | n.d. | healthy | — | A2 | n.d. | 14.47 | 0.09 | 0.08 | 0.08 |
| 4 | n.d. | healthy | — | A2 | n.d. | 27.98 | 0.01 | 0.03 | 0 |
| 5 | M/31 | healthy | — | A2 | − | 25.41 | 0.02 | 0.09 | 0 |
| H7 | M/78 | HAM/TSP | 10 | A1, 3 | + | 22.34 | 0.06 | 0.3 | 0.07 |
| H8 | F/37 | HAM/TSP | 8 | A11, 24 | + | 28.29 | 0.03 | 0.02 | 0.04 |
| H9 | F/49 | HAM/TSP | 10 | A23, 33 | + | 27.77 | 0.02 | 0.02 | 0 |

[1]Carriers were identified among HTLV-1 infected spouses of HAM/TSP patients
[2]CTL activity was previously determined from peripheral blood using Epstein Barr virus immortalized B cells infected with vaccinia expressing the Tax gene as targets (10, 12) and unpublished data.
[3]Percent of cells that stained positive for CD8+ expression and HTLV-1 Tax-A2/Ig
[4]Percent of cells that stained positive for CD8+ expression and HLA-A2/Ig loaded with an irrelevant M1 peptide.
[5]Percent of CD8+ cells that stained positive for Tax-A2/Ig (Background staining using M1-HLA-A2/Ig was subtracted out). All HTLV-1 infected individuals were stained at least twice.
[6]Samples between 1989 to 1998 were tested see FIG. 18.

Table 1
[1] Carriers were identified among HTLV-1 infected spouses of HAM/TSP patients
[2] CTL activity was previously determined from peripheral blood using Epstein Barr virus immortalized B cells infected with vaccinia expressing the Tax gene as targets (10, 12) and unpublished data.
[3] Percent of cells that stained positive for $CD8^+$ expression and HTLV-1 Tax-A2/Ig
[4] Percent of cells that stained positive for $CD8^+$ expression and HLA-A2/Ig loaded with an irrelevant M1 peptide.
[5] Percent of $CD8^+$ cells that stained positive for Tac-A2/Ig (Background staining using M1-HLA-A2Ig was subtracted out). All HTLV-1 infected individuals were stained at least twice.
[6] Samples between 1989 to 1998 were tested see FIG. 18.

References

The following references are expressly incorporated herein.

1. Uchiyama, T., Yodoi, J., Sagawa, K., Takatsuki, K. & Uchino, H. (1977) *Blood* 50, 481–492.
2. Gessain, A, Barin, F., Vernant, J. C., Gout, O., Maurs, L., Calender, A & de Thé, G. (1985) *Lancet* ii, 407–410.
3. Osame, M., Usuku, K., Izumo, S., Ijichi, N., Amitani, H., Igata, A, Matsumoto, M. & Tara, M. (1986) *Lancet* 1, 1031–2.
4. Akizuki, S., Nakazato, O., Higuchi, Y., Tanabe, K., Setoguchi, M., Yoshida, S., Miyazaki, Y., Yamamoto, S., Sudou, S., Sannomiya, K. & et, al. (1987) *Lancet* 1, 156–7.
5. Izumo, S., Usuku, K., Osame, M., Machigashira, K., Johnsonso, M. & Nakagawa, M. (1988) in *The neuropathology of HTLV-I associated myelopathy in Japan: report of an autopsy case and review of the literature*, eds. Roman, G. C., Vernant, J. C. & Osame, M. (Alan R. Liss Inc., New York), pp. 261–267.
6. Hollsberger, P. & Hafler, D. A. (1993) *N Engl J Med* 328, 1173–1182.
7. Itoyama, Y., Minato, S., Kira, J., Goto, I., Sato, H., Okochi, K. & Yamamoto, N. (1988) *Neurology* 38, 816–8.
8. Usuku, K., Sonoda, S., Osame, M., Yashiki, S., Takahashi, K., Matsumoto, M., Sawada, T., Tsuji, K., Tara, M. & Igata, A. (1988) *Ann Neurol*, S143–150.
9. Jacobson, S., Gupta, A., Mattson, D., Mingioli, E. & McFarlin, D. E. (1990) *Ann Neurol* 27, 149–56.
10. Jacobson, S., Shida, H., McFarlin, D. E., Fauci, A. S. & Koenig, S. (1990) *Nature* 348, 245–8.
11. Koenig, S., Woods, R. M., Brewah, Y. A., Newell, A. J., Jones, G. M., Boone, E., Adelsberger, J. W., Baseler, M. W., Robinson, S. M. & Jacobson, S. (1993) *J Immunol* 151, 3874–83.
12. Elovaara, I., Koenig, S., Brewah, A. Y., Woods, R. M., Lehky, T. & Jacobson, S. (1993) *J Exp Med* 177, 1567–73.
13. Jacobson, S., McFarlin, D. E., Robinson, S., Voskuhl, R., Martin, R., Brewah, A., Newell, A. J. & Koenig, S. (1992) *Ann Neurol* 32, 651–7.
14. Levin, M. C., Lehky, T. J., Flerlage, A. N., Katz, D., Kingma, D. W., Jaffe, E. S., Heiss, J. D., Patronas, N., McFarland, H. F. & Jacobson, S. (1997) *N Engl J Med* 336, 839–45.
15. Umehara, F., Izumo, S., Nakagawa, M., Ronquillo, A. T., Takahashi, K., Matsumuro, K., Sato, E. & Osame, M. (1993) *J. Neuropathol. Exp. Neurol* 52, 424–430.
16. Ijichi, S., Eiraku, N., Osame, M., Izumo, S., Kubota, R., Maruyama, I., Matsumoto, M., Niimura, T. & Sonoda, S. (1989) *J Neuroimmunol* 25, 251–4.
17. Jacobson, S., Zaninovic, V., Mora, C., Rodgers, J. P., Sheremata, W. A, Gibbs, C. J., Gajdusek, C. & McFarlin, D. E. (1988) *Ann Neurol*, S196–200.
18. Kubota, R., Kawanishi, T., Matsubara, H., Manns, A & Jacobson, S. (1998) *J Immunol*, in press.
19. Altman, J. D., Moss, P., Goulder, P., Barouch, D. H., McHeyzer, W. M., Bell, J. I., McMichael, A. J. & Davis, M. M. (1996) *Science* 274, 94–6.
20. Dal Porto, J. (1993) *Proc Natl Acad Sci USA* 90, 6671–6675.
21. Biddison, W. E., Kubota, R., Kawanishi, T., Taub, D. D., Cruikshank, W. W., Center, D. M., Connor, E. W., Utz, U. & Jacobson, S. (1997) *J Immunol* 159, 2018–25.
22. Utz, U., Banks, D., Jacobson, S. & Biddison, W. E. (1996) *J Virol* 70, 843–51.
23. Sipsas, N. V., Kalams, S. A., Trocha, A., He, S., Blattner, W. A., Walker, B. D. & Johnson, R. P. (1997) *Journal of Clinical Investigation* 99, 752–62.
24. Imanishi, T., Akaza, T., Kimura, A., Tokunaga, K. & Gojobori, T. (1992) in *Allele haplotype frequencies for HLA-and complement loci in various ethnic groups*, eds. Tsuji, K., Aizawa, M. & Sasazuki, T. (Oxford University Press, Oxford, UK.), pp. 1065–1220.
25. Goulder, P. I., Sewell, A. K., Lalloo, D. G., Price, D. A., Whelan, J. A., Evans, J., Taylor, G. P., Luzzi, G., Giangrande, P., Phillips, R. E. & McMichael, A. J. (1997) *J Exp Med* 185, 1423–33.
26. Van den Eynde, B., van der Bruggen, P. & B (1997) *Curr Opin Immunol* 9, 684–693.
27. Margulies, D. H. (1997) *Curr Opin Immunol* 9, 390–5.
28. Corr, M., Slanetz, A. E., Boyd, L. F., Jelonek, M. T., Khilko, S., al, R. B., Kim, Y. S., Maher, S. E., Bothwell, A. L. & Margulies, D. H. (1994) *Science* 265, 946–9.
29. Matsui, K., Boniface, J. J., Steffner, P., Reay, P. A. & Davis, M. M. (1994) *Proc Natl Acad Sci USA* 91, 12862–6.
30. Sykulev, Y., Brunmark, A., Jackson, M., Cohen, R. J., Peterson, P. A. & Eisen, H. N. (1994) *Immunity* 1, 15–22.
31. Doherty, P. C., Topham, D. J. & Tripp, R. A. (1996) *Immunol Rev* 150, 23–44.
32. Moss, P. A., Rowland, J. S., Frodsham, P. M., McAdam, S., Giangrande, P., McMichael, A. J. & Bell, J. I. (1995) *Proc Natl Acad Sci USA* 92, 5773–7.
33. Lalvani, A., Brookes, R., Hambleton, S., Britton, W. J., Hill, A. & Mcmichael, A. J. (1997) *J Exp Med* 186, 859–865.
34. Pantaleo, G., Koenig, S., Baseler, M., Lane, H. C. & Fauci, A. S. (1990) *J Immunol* 144, 1696–704.
35. Kira, J., Itoyama, Y., Koyanagi, Y., Tateishi, J., Kishikawa, M., Akizuki, S., Kobayashi, I., Toki, N., Sueishi, K., Sato, H. & et, al. (1992) *Ann Neurol* 31, 39–45.
36. Kubota, R., Umehara, F., Izumo, S., Ijichi, S., Matsumuro, K., Yashiki, S., Fujiyoshi, T., Sonoda, S. & Osame, M. (1994) *J Neuroimmunol* 53, 23–9.
37. Hara, H., Morita, M., Iwaki, T., Hatae, T., Itoyama, Y., Kitamoto, T., Akizuki, S., Goto, I. & Watanabe, T. (1994) *J Exp Med* 180, 831–9.
38. Lehky, T. J., Fox, C. H., Koenig, S., Levin, M. C., Flerlage, N., Izumo, S., Sato, E., Raine, C. S., Osame, M. & Jacobson, S. (1995) *Ann Neurol* 37, 167–75.
39. Gessain, A., Saal, F., Giron, M. L., Lasneret, J., Lagaye, S., Gout, O., De, T. G., Sigaux, F. & Peries, J. (1990) *J Gen Virology* 71, 333–41.
40. Moritoyo, T., Reinhart, T. A., Moritoyo, H., Sato, E., Izumo, S., Osame, M. & Haase, A. T. (1996) *Ann Neurol* 40, 84–90.
41. Capon, D. J., S. M. Chamow, J. Mordenti, S. A. Marsters, T. Gregory, H. Mitsuya, R. A. Byrn, C. Lucas, F. M. Wurm, J. E. Groopman, S. Broder, and D. H. Smith. 1989. Designing CD4 immunoadhesins for AIDS therapy *Nature* 337:525–531.
42. Bryn, R. A., J. Mordenti, C. Lucas, D. Smith, S. A. Marsters, J. S. Johnson, P. Cossum, S. M. Chamow, F. M. Wurm, T. Gregory, J. E. Groopman, and D. J. Capon. 1990. Biological Properties of a CD4 Immunoadhesion. *Nature* 344:667–670.
43. Hebell, T., J. M. Ahearn, and D. T. Fearon. 1991. Suppression of the immune response by a soluble complement receptor of B lymphocytes. *Science* 254:102–105.

We claim:

1. A vector encoding a chimeric protein comprising an immunoglobulin heavy chain and an MHC molecule, wherein the immunoglobulin is not IgG-1, wherein the immunoglobulin heavy chain comprises a variable region, wherein the variable region is C-terminal to the MHC molecule.

2. The vector of claim 1 wherein the MHC molecule is an MHC class I molecule.

3. The vector of claim 2 wherein the MHC class I molecule is an HLA class I molecule.

4. The vector of claim 3 wherein the HLA class I molecule is an HLA-A2 molecule.

* * * * *

UNITED STATES PATENT AND TRADEMARK OFFICE
CERTIFICATE OF CORRECTION

PATENT NO. : 6,734,013 B2
DATED : May 11, 2004
INVENTOR(S) : Jonathan Schneck et al.

It is certified that error appears in the above-identified patent and that said Letters Patent is hereby corrected as shown below:

Title page,
Item [56], References Cited, OTHER PUBLICATIONS, please insert the following publication:
-- D. Eilat et al. "Secretion of a soluble, chimeric gamma-delta T-cell receptor-immunoglobulin heterodimer" Proceedings of the National Academy of Sciences, Vol. 89, August 1992, pages 6871-6875 --

Signed and Sealed this

Twenty-fourth Day of May, 2005

JON W. DUDAS
*Director of the United States Patent and Trademark Office*